US012728161B2

(12) United States Patent
Aguilar-Carreno et al.

(10) Patent No.: US 12,728,161 B2
(45) Date of Patent: Sep. 8, 2026

(54) USE OF MEMBRANE INHIBITORS TO ENHANCE VACCINE DEVELOPMENT AGAINST ENVELOPED VIRUSES

(71) Applicant: CORNELL UNIVERSITY, Ithaca, NY (US)

(72) Inventors: Hector Aguilar-Carreno, Ithaca, NY (US); Isaac Monreal, Ithaca, NY (US); David Buchholz, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 989 days.

(21) Appl. No.: 17/774,632

(22) PCT Filed: Nov. 6, 2020

(86) PCT No.: PCT/US2020/059425
§ 371 (c)(1),
(2) Date: May 5, 2022

(87) PCT Pub. No.: WO2021/092392
PCT Pub. Date: May 14, 2021

(65) Prior Publication Data
US 2022/0401554 A1 Dec. 22, 2022

Related U.S. Application Data

(60) Provisional application No. 62/932,309, filed on Nov. 7, 2019.

(51) Int. Cl.
*A61K 39/29* (2006.01)
*A61K 31/13* (2006.01)
(Continued)

(52) U.S. Cl.
CPC .............. *A61K 39/29* (2013.01); *A61K 31/13* (2013.01); *A61K 31/196* (2013.01);
(Continued)

(58) Field of Classification Search
CPC ...... A61K 39/29; A61K 31/13; A61K 31/196; A61K 31/265; A61K 31/351;
(Continued)

(56) References Cited

U.S. PATENT DOCUMENTS 7,101,676 B2 9/2006 Buechter et al.
8,613,934 B2 12/2013 Raviv et al.
(Continued)

FOREIGN PATENT DOCUMENTS

CN 110117238 A 8/2019
WO 90/07952 A1 7/1990
(Continued)

OTHER PUBLICATIONS

Garcia et al.; Mode of inactivation of arenaviruses by disulfide-based compounds; Antiviral Research, 55, 2002, 437-446. (Year: 2002).*

(Continued)

*Primary Examiner* — Sarah Pihonak
*Assistant Examiner* — Jackson J Hernandez
(74) *Attorney, Agent, or Firm* — Troutman Pepper Locke LLP (Rochester)

(57) ABSTRACT

The present application relates to method of vaccinating a subject against infection by an enveloped virus. The method includes providing a compound of the Formula (I) as described herein, and contacting the compound of Formula (I) with an isolated enveloped virus, having a membrane, to inactivate the membrane of the isolated enveloped virus. The subject is then treated with the enveloped virus having an inactivated membrane to vaccinate the subject against the enveloped virus. Further disclosed is an ex vivo vaccine composition including the compound of Formula (I) and an enveloped virus.

10 Claims, 14 Drawing Sheets

Specification includes a Sequence Listing.

XM-01 XM-02 XM-03 XM-04 XM-05
XM-06 XM-07 XM-08 XM-09 XM-10
XM-11 XM-12 XM-13 XM-14 XM-15
LJ001 GYY4137

(51) Int. Cl.

| | |
|---|---|
| ***A61K 31/196*** | (2006.01) |
| ***A61K 31/265*** | (2006.01) |
| ***A61K 31/351*** | (2006.01) |
| ***A61K 31/407*** | (2006.01) |
| ***A61K 31/4164*** | (2006.01) |
| ***A61K 31/427*** | (2006.01) |
| ***A61K 31/43*** | (2006.01) |
| ***A61K 31/4709*** | (2006.01) |
| ***A61K 31/496*** | (2006.01) |
| ***A61K 31/4965*** | (2006.01) |
| ***A61K 31/522*** | (2006.01) |
| ***A61K 31/546*** | (2006.01) |
| ***A61K 31/575*** | (2006.01) |
| ***A61K 31/65*** | (2006.01) |
| ***A61K 31/662*** | (2006.01) |
| ***A61K 31/7048*** | (2006.01) |
| ***A61K 31/7056*** | (2006.01) |
| ***A61K 31/7072*** | (2006.01) |
| ***A61K 31/7076*** | (2006.01) |
| ***A61K 38/14*** | (2006.01) |
| ***A61K 38/21*** | (2006.01) |
| ***A61K 39/12*** | (2006.01) |
| ***A61K 39/145*** | (2006.01) |
| ***A61K 39/155*** | (2006.01) |
| ***A61K 39/205*** | (2006.01) |
| ***A61K 39/21*** | (2006.01) |
| ***A61K 39/215*** | (2006.01) |
| ***A61K 39/245*** | (2006.01) |
| ***A61K 39/275*** | (2006.01) |
| ***A61P 31/14*** | (2006.01) |
| ***A61P 31/16*** | (2006.01) |
| ***A61P 31/22*** | (2006.01) |
| *A61K 39/00* | (2006.01) |

(52) U.S. Cl.

CPC .......... *A61K 31/265* (2013.01); *A61K 31/351* (2013.01); *A61K 31/407* (2013.01); *A61K 31/4164* (2013.01); *A61K 31/427* (2013.01); *A61K 31/43* (2013.01); *A61K 31/4709* (2013.01); *A61K 31/496* (2013.01); *A61K 31/4965* (2013.01); *A61K 31/522* (2013.01); *A61K 31/546* (2013.01); *A61K 31/575* (2013.01); *A61K 31/65* (2013.01); *A61K 31/662* (2013.01); *A61K 31/7048* (2013.01); *A61K 31/7056* (2013.01); *A61K 31/7072* (2013.01); *A61K 31/7076* (2013.01); *A61K 38/14* (2013.01); *A61K 38/212* (2013.01); *A61K 39/12* (2013.01); *A61K 39/145* (2013.01); *A61K 39/155* (2013.01); *A61K 39/205* (2013.01); *A61K 39/21* (2013.01); *A61K 39/215* (2013.01); *A61K 39/245* (2013.01); *A61K 39/275* (2013.01); *A61P 31/14* (2018.01); *A61P 31/16* (2018.01); *A61P 31/22* (2018.01); *A61K 2039/5252* (2013.01); *A61K 2039/55505* (2013.01); *A61K 2039/55511* (2013.01); *A61K 2039/5555* (2013.01); *A61K 2039/55561* (2013.01); *A61K 2039/55566* (2013.01); *A61K 2039/55572* (2013.01); *A61K 2039/55583* (2013.01)

(58) Field of Classification Search

CPC .............. A61K 31/407; A61K 31/4164; A61K 31/427; A61K 31/43; A61K 31/4709; A61K 31/496; A61K 31/4965; A61K 31/522; A61K 31/546; A61K 31/575; A61K 31/65; A61K 31/662; A61K 31/7048; A61K 31/7056; A61K 31/7072; A61K 31/7076; A61K 38/14; A61K 38/212; A61K 39/12; A61K 39/145; A61K 39/155; A61K 39/205; A61K 39/21; A61K 39/215; A61K 39/245; A61K 39/275; A61K 2039/5252; A61K 2039/55505; A61K 2039/55511; A61K 2039/5555; A61K 2039/55561; A61K 2039/55566; A61K 2039/55572; A61K 2039/55583; A61P 31/14; A61P 31/16; A61P 31/22; A61P 31/12; C12N 2760/16134; C12N 2770/20034; C12N 7/00

See application file for complete search history.

(56) References Cited

U.S. PATENT DOCUMENTS

| | | | |
|---|---|---|---|
| 9,096,504 | B2 | 8/2015 | Xian et al. |
| 2004/0253272 | A1 | 12/2004 | Kaneda |
| 2006/0257852 | A1 | 11/2006 | Rappuoli et al. |
| 2009/0297558 | A1 | 12/2009 | Raviv et al. |
| 2012/0219613 | A1 | 8/2012 | Lee et al. |
| 2014/0037684 | A1 | 2/2014 | Pasteur |
| 2014/0322361 | A1 * | 10/2014 | Gojon-Romanillos et al. |
| 2016/0160178 | A1 | 6/2016 | Harrelson et al. |
| 2018/0271823 | A1 | 9/2018 | Aguilar-Carreno et al. |
| 2019/0099484 | A1 | 4/2019 | Garcia-Sastre et al. |
| 2019/0358192 | A1 | 11/2019 | Aguilar-Carreno et al. |

FOREIGN PATENT DOCUMENTS

| | | | |
|---|---|---|---|
| WO | 96/09406 | A1 | 3/1996 |
| WO | WO2012075242 | A2 * | 6/2012 |

OTHER PUBLICATIONS

Bazhanov et al.; Broad-Range Antiviral Activity of Hydrogen Sulfide Against Highly Pathogenic RNA Viruses; Scientific Reports, 2017, 7, 41029, 12 pages. (Year: 2017).*

International Search Report and Written Opinion for corresponding Application No. PCT/US2020/059425 (mailed Apr. 1, 2021).

Balmer et al., "Broad-Spectrum Antiviral JL122 Blocks Infection and Inhibits Transmission of Aquatic Rhabdoviruses," Virol. 525:143-149 (2018).

Pubchem, Compound Summary for CID 12569, Create Date Mar. 26, 2005 (https:/pubchem.ncbi.nim.nih.gov/compound/12569).

Xiao et al., "Polysulfurating Reagent Design for Unsymmetrical Polysulfide Construction," Nat. Comm. 9:1-9 (2018).

Citi et al., "Anti-Inflammatory and Antiviral Roles of Hydrogen Sulfide: Rationale for Considering H(2)S Donors in COVID-19 Therapy," Br. J. Pharmacol. 1-11 (2020).

Contreras, "Effect of Membrane Composition on Viral Entry and Egress," (abstract only) Cornell Theses and Dissertations (2020).

Pacheco, "Sulfur-Containing Compounds as Hydrogen Sulfide Donors and Broad-Spectrum Antiviral Agents," Dissertation, Washington State University (2017).

Pacheco, "Sulfur-Containing Compounds as Hydrogen Sulfide Donors and Broad-Spectrum Antiviral Agents," (preview) Dissertation, Washington State University (2017).

Pan et al. ,"Disulfide Formation via Sulfenamides," Chem. Commun. 47:352-354 (2011).

Rice et al., "Evaluation of Selected Chemotypes in Coupled Cellular and Molecular Target-Based Screens Identifies Novel HIV-1 Zinc Finger Inhibitors," J. Med. Chem. 39:3606-3616 (1996).

Zhao et al., "Controllable Hydrogen Sulfide Donors and the Activity Against Myocardial Ischemia-Reperfusion Injury," ACS Chem. Biol. 8(6):1283-1290 (2013).

Balmer et al., "Inhibition of an Aquatic Rhabdovirus Demonstrates Promise of a Broad-Spectrum Antiviral for Use in Aquaculture," J. Virol. 91(4):e02181-16 (2017).

(56) References Cited

OTHER PUBLICATIONS

Vigant et al., "Broad-Spectrum Antivirals Against Viral Fusion," Nat. Rev. Microbiol. 13(7):426-437 (2015).
Vigant et al., "A Mechanistic Paradigm for Broad-Spectrum Antivirals that Target Virus-Cell Fusion," PLOS Pathogens 9(4):e1003297 (2013).
Wolf et al., "A Broad-Spectrum Antiviral Targeting Entry of Enveloped Viruses," PNAS 107(7):3157-3162 (2010).
Wolf et al., "SI Pharmacokinetic Methodology," Supporting Information PNAS 2-10 (10.1073/pnas.0909587107).
International Preliminary Report on Patentability for PCT/US2020/059425, mailed May 16, 2022.
European Search Report and Written Opinion in EP Application No. 20886009.8 (dated Nov. 7, 2023).
Chu et al., "Enhanced Stability of Inactivated Influenza Vaccine Encapsulated in Dissolving Microneedle Patches," Pharm. Res. 33(4):868-878 (2016) [Author Manuscript].
Bonafe et al., "Virus Inactivation by Anilinonaphthalene Sulfonate Compounds and Comparison with Other Ligands," Biochem. Biophys. Re. Comm. 275(3):955-961 (2000).
Gupta et al., "Inactivation of Non-Enveloped Virus by 1,5 Iodonaphthyl Azide," BMC Res. Notes 8:44 (2015).
Raviv et al., "Inactivation of Retroviruses with Preservation of Structural Integrity by Targeting the Hydrophobic Domain of the Viral Envelope," J. Virol. 79(19):12394-12400 (2005).
Stauffer et al., "Inactivation of Vesicular Stomatitis Virus through Inhibition of Membrane Fusion by Chemical Modification of the Viral Glycoprotein," Antiviral. Res. 73(1):31-39 (2007).
Lenard et al., "Photodynamic Inactivation of Infectivity of Human Immunodeficiency Virus and other Enveloped Viruses using Hypericin and Rose Bengal: Inhibition of Fusion and Syncytia Formation," Proc. Natl. Acad. Sci. USA 90:158-162 (1993).
Raviprakash et al., "Dengue Virus Photo-Inactivated in Presence of 1,5-lodonaphthylazide (INA) or AMT, a Psoralen Compound (4'-aminomethyl-trioxsalen) is Highly Immunogenic in Mice," Hum. Vaccin. Immunother. 9 (11):2336-2341 (2013).
Boyd et al., "Discovery of Cyanovirin-N, a Novel Human Immunodeficiency Virus-Inactivating Protein That Binds Viral Surface Envelope Glycoprotein gp120: Potential Applications to Microbicide Development," Antimicrob. Agents Chemother. 41(7):1521-1530 (1997).
Astill et al., "Examination of the Effects of Virus Inactivation Methods on the Induction of Antibody••-and cell-•-Mediated Immune Responses Against Whole Inactivated H9N2 avian Influenza Virus Vaccines in Chickens," Vaccine 36(27):3908-3916 (2018).
Jonges et al., "Influenza Virus Inactivation for Studies of Antigenicity and Phenotypic Neuraminidase Inhibitor Resistance Profiling," J. Clin. Microbiol. 48(3):928-940 (2010).
Delrue et al., "Inactivated Virus Vaccines from Chemistry to Prophylaxis: Merits, Risks and Challenges," Expert. Rev. Vaccines 11(6):695-719 (2012).

* cited by examiner

XM-01 XM-02 XM-03 XM-04 XM-05

XM-06 XM-07 XM-08 XM-09 XM-10

XM-11 XM-12 XM-13 XM-14 XM-15

LJ001 GYY4137

```
                           SEQUENCE LISTING


<160> NUMBER OF SEQ ID NOS: 1

<210> SEQ ID NO 1
<211> LENGTH: 36
<212> TYPE: PRT
<213> ORGANISM: Artificial Sequence
<220> FEATURE:
<223> OTHER INFORMATION: HR2 peptide

<400> SEQUENCE: 1

Lys Val Asp Ile Ser Ser Gln Ile Ser Ser Met Asn Gln Ser Leu Gln
1               5                   10                  15

Gln Ser Lys Asp Tyr Ile Lys Glu Ala Gln Arg Leu Leu Asp Thr Val
            20                  25                  30

Asn Pro Ser Leu
        35
```

USE OF MEMBRANE INHIBITORS TO ENHANCE VACCINE DEVELOPMENT AGAINST ENVELOPED VIRUSES

This application is a national stage application under 35 U.S.C. § 371 of International Application No. PCT/US2020/059425, filed Nov. 6, 2020, which claims the benefit of U.S. Provisional Patent Application Ser. No. 62/932,309 filed Nov. 7, 2019, which are hereby incorporated by reference in its their entirety.

This invention was made with government support under AI109022, and EB023860 awarded by the National Institutes of Health. The government has certain rights in the invention.

FIELD

The present application relates to an ex vivo vaccine composition of enveloped viruses, and a method of vaccinating a subject against infection by an enveloped virus.

BACKGROUND

In 2015, the World Health Organization (WHO) produced a list of emerging pathogens most likely to cause major epidemics worldwide that require urgent research and development. Notably, all pathogens included were enveloped viruses (Crimean Congo hemorrhagic fever, Ebola, Marburg, Lassa fever, MERS, SARS, Nipah, and Rift Valley fever viruses) (Black, C., "Blueprint for R&D Preparedness and Response to Public Health Emergencies Due to Highly Infectious Pathogens," Workshop on Prioritization of Pathogens (Word Health Organization, Geneva, Switzerland, December 2015); W. H. Organization. (© Copyright World Health Organization (WHO) (2017)). Further, most of these human viruses are zoonotic (transmitted from animals). The National Academy of Sciences also stated that zoonotic diseases are a leading cause of illness and death worldwide, in addition to negatively affecting the global economy, as exemplified by the recent SARS-CoV-2 virus pandemic (Realman et al., "Microbial Evolution and Co-adaptation: A Tribute to the Life and Scientific Legacies of Joshua Lederberg," (2009)). Thus, therapeutics effectively and broadly targeting viral membranes may become invaluable antiviral agents.

Collectively, the number of antiviral therapeutics is limited. Of all the infectious human viruses, currently only nine have approved antivirals (HBV, HCV, HCMV, HIV, HSV, HPV, RSV, VZV, and IAV) (De Clercq and Li, "Approved Antiviral Drugs over the Past 50 Years," *Clin. Microbiol. Rev.* 29:695-747 (2016)). Current approaches to antiviral development generally focus on individual pathogens targeting precise functions such as protein-protein interactions, enzymatic activities of key proteins, or viral replication, leading to treatments with limited therapeutic ranges. For example, ribavirin treatment of hepatitis C and RSV infections has been approved in many countries including the U.S. However, data for the clinical efficacy of ribavirin against influenza virus is limited due to small sample sizes, incomplete trial information, and/or incompatible protocols for meta analysis (Schaefer et al., "Adherence and Mental Side Effects During Hepatitis C Treatment with Interferon Alfa and Ribavirin in Psychiatric Risk Groups," *Hepatology* 37:443-451 (2003)). Ribavirin and Remdesivir have also been used to treat paramyxoviral infections (Leyssen et al., "The Predominant Mechanism by Which Ribavirin Exerts its Antiviral Activity in vitro Against Flaviviruses and Paramyxoviruses is Mediated by Inhibition of IMP Dehydrogenase," *J. Virol.* 79:1943-1947 (2005); W. W. H. Organization, "(WHO) World Health Organization Guidelines for Pharmacological Management of Pandemic Influenza A(H1N1) 2009 and Other Influenza Viruses," (2010); Lo et al., "Remdesivir (GS-5734) Protects African Green Monkeys from Nipah Virus Challenge," *Sci. Transl. Med.* 11 (2019)). Arbidol has been used against influenza virus in Russia and China; however, its use in the U.S. is not FDA approved, since side effects are unclear despite low toxicity claims (W. W. H. Organization, "(WHO) World Health Organization Guidelines for Pharmacological Management of Pandemic Influenza A(H1N1) 2009 and Other Influenza Viruses," (2010); Haviernik et al., "Arbidol (Umifenovir): A Broad-Spectrum Antiviral Drug That Inhibits Medically Important Arthropod-Borne Flaviviruses," *Viruses* 10(4): 184 (2018)). However, compared to nucleotide/nucleoside analog pro-drugs or drugs that alter protein conformations, compounds that target the viral membrane stand a better chance as effective broad-spectrum antivirals. There are several potential broad-spectrum antivirals in early stages of research, including the membrane inhibitor LJ001 and the hydrogen sulfide ($H_2S$)-producing GYY4137, which have shown inhibitory properties against respiratory syncytial virus (RSV), human metapneumovirus (hMPV) and Nipah virus (NiV) (Leyssen et al., "The Predominant Mechanism by Which Ribavirin Exerts its Antiviral Activity in vitro Against Flaviviruses and Paramyxoviruses is Mediated by Inhibition of IMP Dehydrogenase," *J. Virol.* 79:1943-1947 (2005); Vigant et al., "A Mechanistic Paradigm for Broad-Spectrum Antivirals that Target Virus-Cell Fusion," *Plos Pathog.* 9(4):e1003297 (2013); Li et al., "Role of Hydrogen Sulfide in Paramyxovirus Infections," *J. Virol.* 89:5557-5568 (2015)). However, these antivirals face technical obstacles for their practical use in vivo. LJ001 requires light in order to produce singlet oxygen, which in turn destabilizes the viral membrane. This is a desirable trait for applications in aquaculture, but a limitation for human or animal use (Vigant et al., "A Mechanistic Paradigm for Broad-Spectrum Antivirals that Target Virus-Cell Fusion," *Plos Pathog.* 9(4):e1003297 (2013); Wolf et al., "A Broad-spectrum Antiviral Targeting Entry of Enveloped Viruses," *PNAS* 107:3157-3162 (2010); Balmer et al., "Broad-Spectrum Antiviral JL122 Blocks Infection and Inhibits Transmission of Aquatic Rhabdoviruses," *Virology* 525:143-149 (2018)).

The present application is directed to overcoming these and other deficiencies in the art.

SUMMARY

The present application relates to a method of vaccinating a subject against infection by an enveloped virus. The method includes:

providing a compound of the Formula (I):

(I)

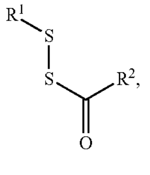

wherein $R^1$ is

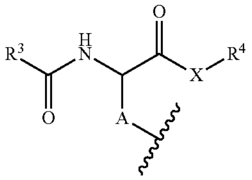

or —C(O)Ph, $R^2$ is $C_{1-6}$ alkyl or aryl;

$R^3$ is $C_{1-6}$ alkyl or aryl;

$R^4$ is $C_{1-6}$ alkyl optionally substituted with aryl;

A is $C_{1-3}$ alkylene;

X is O or NH; and

is the point of attachment of $R^1$ to S;

contacting the compound of Formula (I) with an isolated enveloped virus, having a membrane, to inactivate the membrane of the isolated enveloped virus; and treating the subject with the enveloped virus having an inactivated membrane to vaccinate the subject against the enveloped virus.

Another aspect of the present application relates to an ex vivo vaccine composition including:

one or more isolated enveloped viruses and a compound of the Formula (I):

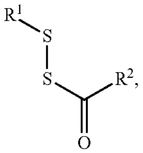

(I)

wherein $R^1$ is

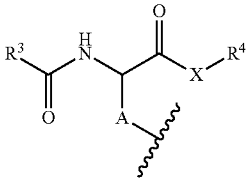

or —C(O)Ph, $R^2$ is $C_{1-6}$ alkyl or aryl;

$R^3$ is $C_{1-6}$ alkyl or aryl;

$R^4$ is $C_{1-6}$ alkyl optionally substituted with aryl;

A is $C_{1-3}$ alkylene;

X is O or NH; and

is the point of attachment of $R^1$ to S, wherein the compound is present in the vaccine composition in an amount sufficient to inactivate said one or more isolated enveloped viruses.

In the search for broad-spectrum antivirals, a library of $H_2S$ releasing and related sulfur-containing compounds was analyzed to serve as controllable $H_2S$ donors. These included compounds that contained disulfide bonds (O'Gara et al., "Activities of Garlic Oil, Garlic Powder, and Their Diallyl Constituents Against *Helicobacter pylori,*" *Appl. Environ. Microbiol.* 66:2269-2273 (2000); Zhao et al., "Cysteine-Activated Hydrogen Sulfide (H2S) Donors," *J. Am. Chem. Soc.* 133:15-17 (2011); Park et al., "Synthesis and Evaluation of Phosphorodithioate-Based Hydrogen Sulfide Donors," *Mol. Biosyst.* 9:2430-2434 (2013); Zhao et al., "Controllable Hydrogen Sulfide Donors and Their Activity Against Myocardial Ischemia-Reperfusion Injury," *ACS Chem. Biol.* 8:1283-1290 (2013); Zhao et al., "Thiol-Activated Gem-Dithiols: A New Class of Controllable Hydrogen Sulfide Donors," *Org. Lett.* 16:4536-4539 (2014); Kang et al., "pH-Controlled Hydrogen Sulfide Release for Myocardial Ischemia-Reperfusion Injury," *J. Am. Chem. Soc.* 138:6336-6339 (2016); Xu et al., "Ammonium Tetrathiomolybdate as a Water-soluble and Slow-Release Hydrogen Sulfide Donor," *Bioorg. Med. Chem. Lett.* 26:1585-1588 (2016); Marchese et al., "Antifungal and Antibacterial Activities of Allicin: A Review," *Trends Food Sci. Technol.* 52:49-56 (2016), which is hereby incorporated by reference in its entirety). Similar compounds, found in garlic, have antiviral, antibacterial, and antifungal properties and are claimed to be natural antibiotics (Weber et al., Invitro "Virucidal Effects of *Allium-Sativum* (Garlic) Extract and Compounds," *Planta Medica* 58:417-423 (1992); Tsai et al., "Antiviral Properties of Garlic—In vitro Effects on Influenza B, Herpes-Simplex and Coxsackie-Viruses," *Planta Medial* 51:460-461 (1985); Iciek et al., "Biological Properties of Garlic and Garlic-Derived Organosulfur Compounds," *Environ. Mol. Mutagen.* 50:247-265 (2009), which are hereby incorporated by reference in their entirety). NaHS and GYY4137, were also included as $H_2S$-donor compounds with known antiviral effects against NiV, although at high (millimolar) concentrations (Li et al., "Role of Hydrogen Sulfide in Paramyxovirus Infections," *J. Virol.* 89:5557-5568 (2015), which is hereby incorporated by reference in its entirety).

The search produced a new class of antiviral compounds that target a critical step in viral infections: membrane fusion, which is essential for entry of enveloped viruses into host cells. It was found that one of the lead compounds, XM-01, which contains acyl disulfide bonds, inhibited viral entry of several important enveloped viruses at low micromolar concentrations. XM-01 intercalates deep into the hydrophobic region of lipid bilayers, decomposes into polysulfides, and subsequently forms perthiyl radicals that interact with the membrane to increase membrane order and phase transition temperature. The targeting of membranes renders these compounds less likely to induce viral resistance. Furthermore, it was found that XM compounds leave the glycoproteins in their native conformations. These highly desirable characteristics led to testing the use of these compounds as effective enveloped virus inactivators for vaccine development. Mice vaccinated with a XM-01 inactivated Ca/04/2009 H1N1 influenza virus vaccine were completely protected upon homologous viral challenge. This coincided with a stronger humoral response and reduced morbidity and mortality as compared to traditional formalin inactivated vaccination approaches. Further, the XM-01 inactivated virions displayed an adjuvantation effect, inducing innate immunity in vitro. This suggests that XM compounds can generate more effective inactivated-virus vaccines than current pharmacologically used methods. Herein, it is demonstrated XM compounds have the ability to be broad-spectrum anti-enveloped virus inactivators with potential in vaccine development.

BRIEF DESCRIPTION OF THE DRAWINGS

FIG. 1A shows the structures of the compounds tested (XM-numbers 01-15), as well as, control compounds LJ001 and GYY4137, which are known to inhibit enveloped viruses and NiV, respectively. FIG. 1B is a graphical representation of the percent infectivity of pNiV in Vero cells. The compounds tested were used at 10 μM concentrations. FIG. 1C is a graphical representation of the percent cell viability following the incubation of Vero cells with the best compounds (from FIG. 1B) determined using a CCK-8 kit to measure the dehydrogenase activity of live cells.

FIG. 2C is a plot depicting XM-01 inhibition of enveloped virus infection at various concentrations. The virions were treated with XM-01 before infection. XM-01 inhibits pNiV, HSV-1, RSV, HCMV, VSV, and influenza virus infections. FIGS. 2D and 2E are graphical representation of the percent infectivity of rotavirus (FIG. 2D) and norovirus (FIG. 2E). XM-01 lack of inhibition of rotavirus and norovirus infections. The rotavirus inhibitor control GRA (25 μg/ml) and IFNα (1000 U/ml) are shown. Three experiments were performed for each sub-FIG. 2A-2E. All data shown are means of at least triplicate experiments with the standard errors. Infectivity of HSV-1, RSV, and influenza were quantified by plaque assays. Infectivity of VSV and NiV were quantified with *Renilla* luciferase reporters. The infectivity of HCMV was quantified by GFP expression.

FIG. 3A is a graphical depiction of the percent infectivity of pNiV treated with a control, LJ001, and XM-01. Dilutions of pNiV pre-treated with XM-01 for 30 min and cleared of excess XM-01 by ultracentrifugation before Vero cell infections. LJ001 was used as a control. FIG. 3B is a plot of the difference in infectivity of the treatment of cell with XM-01 before virus treatment in comparison to the pre-treatment of the virons with XM-01. Vero cells were pre-treated with XM-01 for 30 min and washed with warm PBS 3 times, followed by pNiV infection (top line), as compared with pre-treatment of virions as done in FIG. 3A (bottom line). FIG. 3C is a graph of luciferase activity of cells with the addition of XM-01 at various times post-infection. This shows inhibition early in the infection process. FIG. 3D is a graphical representation of the infection of Vero cells by pseudotyped NiV pre-treated with XM-01 before infecting Vero cells in the darkness. While XM-01 does not need light to inhibit the infections, LJ001 does. (N=3).

FIGS. 4A-4B are graphical representations of the percent normalized mean fluorescence intensity (MFI) for cells treated with a DMSO control or XM-01. XM-01 at 10 μM and soluble receptor ephrinB2 were incubated with cells expressing NiV G glycoprotein for 30 min. XM-01 did not affect receptor binding to G on PK13 cells (FIG. 4A) or 293T cells (FIG. 4B). The values for the negative control, PcDNA3.1+ transfected cells, not expressing G, were subtracted from the experimental values. FIG. 4C is a graphical representation of the MFI showing that XM-01 at 10 μM did not interfere with the triggering of the NiV F protein in the fusion cascade process. FIG. 4D is a graphical representation showing the percent syncytia of cells treated with XM-01 at 10 μM or the control membrane fusion inhibitor LJ001 at 1 μM. Both the control and XM-01 affect cell-cell fusion. FIG. 4E is a graphical representation of the protein expression, showing XM-01 did not affect glycoprotein F and G expression, using anti-Flag and anti-HA tag antibodies, respectively. FIG. 4F is a graphical representation of the percent normalized MFI, showing XM-01 did not significantly affect conformation changes of protein G or F (N=3). All data shown are means of at least triplicate experiments with standard deviation. Statistical significance was determined with one-sample t-tests and are denoted by *, $P<0.05$ and **, $P<0.01$.

FIG. 5A is electron microscopy images of treated pNiV. The black arrows indicate affected membranes and white arrows indicate spilled RNA. The Virions were treated with DMSO (0.1%) vehicle control, LJ001 membrane inhibitory control, and XM-01. FIG. 5B is a graph of the luminescence of nsp3: luciferase RNA construct after XM-01 treatment and electroporation into BHK cells. DC=Decapped. The statistical significance was determined with a t-test. FIG. 5C is a comparison of ESR spectra in POPC/POPG (4:1) MLV without (black) or with (gray) 5% XM-01 (mol:mol ratio) binding. At 25° C., the high field peak of the spectrum upon XM-01 binding shifted toward lower frequency, indicating that the spin of 16PC was in a more hydrophobic environment. The equivalent comparison of the spectra with or without XM-01 was collected at 20° C. further demonstrated a second component emerging upon XM-01 binding (black arrow). Thus, the spectra clearly indicate that XM-01 intercalates into the deep hydrophobic region of the membrane. FIG. 5D is a plot of the change in standard molar entropy, showing that XM-01 causes an increase in membrane order at various lipid ratios. FIG. 5E is a graphical representation of the phase transition temperature, showing XM-01 increased the phase transition temperature of both pure POPC and POPC/POPG (4:1) membranes, (right) without (black) or with (gray) XM-01. $P<0.005$. All experiments were performed in 5 mM HEPES, 10 mM MES, 150 mM NaCl buffer at pH 7. Each experiment was repeated two to three times, and a representative of each type of experiment is shown. FIG. 5F shows the reaction between butylamine and XM-01, which decomposes XM-01, creating disulfide and polysulfide molecules; subsequently, perthiyl radicals are formed. FIG. 5G is the mass spectrum of XM-01 treated with butylamine, which revealed the formation of disulfide and polysulfide products. This indicates the presence of the persulfide intermediate (RSSH) from XM-01.

FIG. 6A is the graphical representation of the results of the plaque assays of MDCK cells infected with Ca/04/09 H1N1 pretreated with increasing concentrations of XM-01 for 4 hours at room temperature. The data shown is an average of two independent experiments (N=2). FIG. 6B is a plot of the percent survival of vaccinated mice after challenge with 5 $LD_{50}$ of Ca/04/09 H1N1. There were 5 mice in each group. FIG. 6C is a plot of the percent weight change after Ca/04/09 H1N1 challenge in vaccinated mice. FIG. 6D is a graphical representation of the hemagglutination inhibition assay with serum from vaccinated mice. FIG. 6E is a plot of the percent neuraminidase activity assay with serum from vaccinated mice. Statistical significance determined with t-tests and are denoted by *, $P<0.05$ and **, $P<0.01$.

FIG. 7A is a plot of the percent weight change in female mice. FIG. 7B is a plot of the percent weight change in male mice.

FIG. 8A is the graphical representation of female mice serum HA inhibition after the first vaccination boost. FIG. 8B is the graphical representation of Female mice serum HA inhibition after second vaccination boost. FIG. 8C is the graphical representation of male mice serum HA inhibition after second vaccination boost. Statistical significance determined with one-sample t-tests and is denoted by *, $P<0.05$.

FIG. 9A is a plot of the neuraminidase activity in female mice serum after the first vaccination boost. FIG. 9B is a plot of the neuraminidase of female mice serum activity after second vaccination boost. FIG. 9C is a plot of the NA activity of male mice serum after second vaccination boost. Statistical significance determined with one-sample t-tests and is denoted by *, $P<0.05$.

DETAILED DESCRIPTION

Figure 1A:
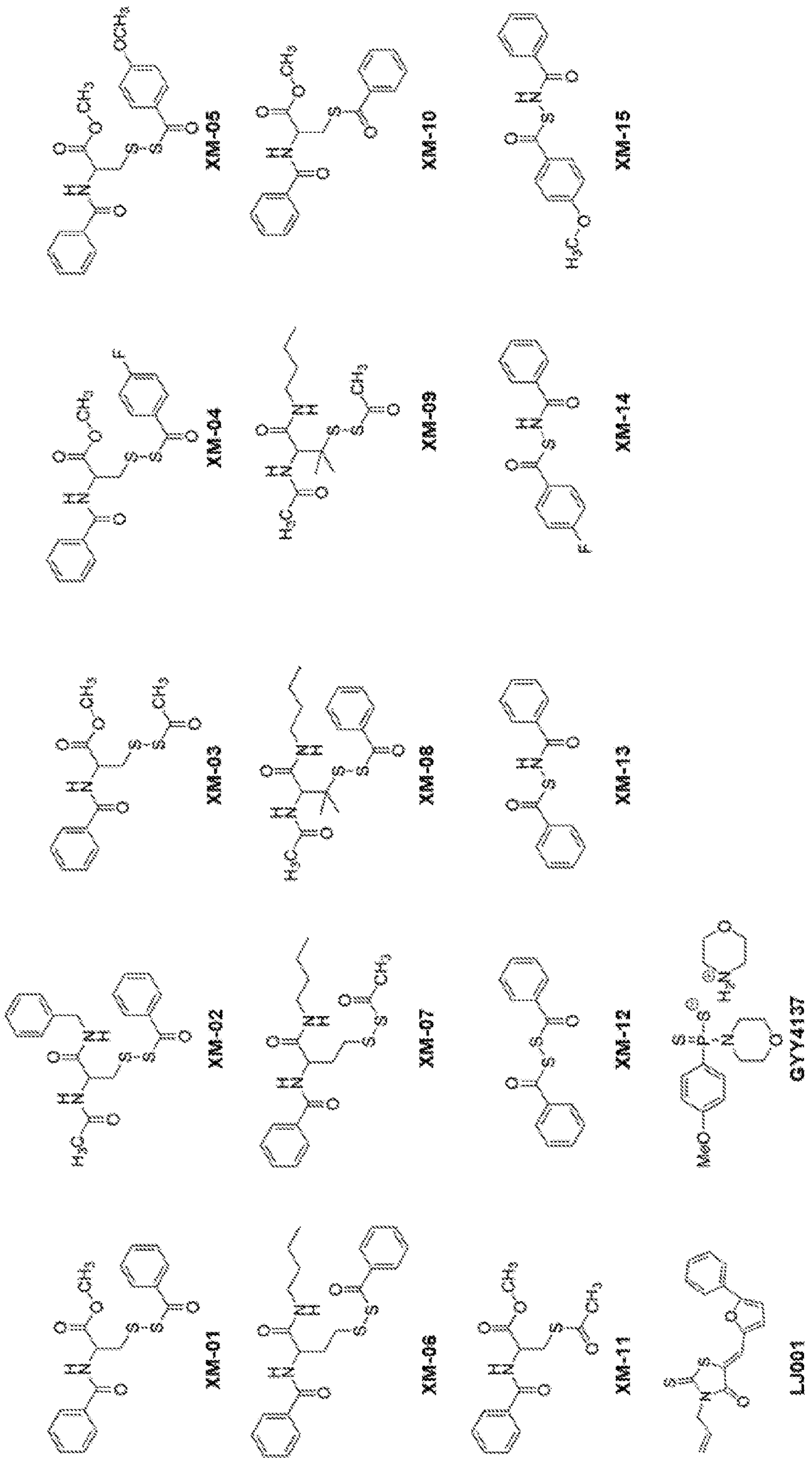
FIGS. 1A-1C depict that compound XM-01 strongly inhibited pseudotyped NiV infections at low cytotoxicity levels.

The present application relates to a method of vaccinating a subject against infection by an enveloped virus. The method includes:

providing a compound of the Formula (I):

(I)

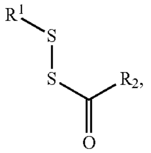

wherein $R^1$ is

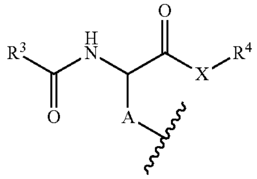

or —C(O)Ph, $R^2$ is $C_{1-6}$ alkyl or aryl;

$R^3$ is $C_{1-6}$ alkyl or aryl;

$R^4$ is $C_{1-6}$ alkyl optionally substituted with aryl;

A is $C_{1-3}$ alkylene;

X is O or NH; and

is the point of attachment of $R^1$ to S;

contacting the compound of Formula (I) with an isolated enveloped virus, having a membrane, to inactivate the membrane of the isolated enveloped virus; and treating the subject with the enveloped virus having an inactivated membrane to vaccinate the subject against the enveloped virus.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Branched means that one or more lower alkyl groups such as methyl, ethyl, or propyl are attached to a linear alkyl chain. Exemplary alkyl groups include methyl, ethyl, n-propyl, propyl, n-butyl, t-butyl, n-pentyl, 3-pentyl, and the like.

The term "alkylene" refers to a divalent group formed from an alkane by removal of two hydrogen atoms. Exemplary alkylene groups include, but are not limited to, divalent groups derived from the alkanes described above The term "aryl" means an aromatic monocyclic or multicyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

"Unsubstituted" atoms bear all of the hydrogen atoms dictated by their valency.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. When a substituent is keto (i.e., =O), then two hydrogens on the atom are replaced. Combinations of substituents and/or variables are permissible only if such combinations result in stable compounds. A "stable compound" is meant to be a compound that is sufficiently robust to survive isolation to a useful degree of purity from a reaction mixture, and formulation into an efficacious therapeutic agent.

One embodiment of the present application relates to the compound Formula (I), where A is —$CH_2$—$CH_2$—, X is NH, $R^4$ is n-butyl, and $R^2$ is not methyl.

A further embodiment of the present application relates to a compound Formula (I), where if $R^1$ is —C(O)Ph, then $R^2$ is aryl.

In another embodiment of the present application, in the compound Formula (I), $R^2$ is Me or Ph. In a further embodiment of the compound of Formula (I), $R^3$ is Me or Ph. In another embodiment of the compound of Formula (I), $R^4$ is Me, —$CH_2$-Ph, or n-butyl.

Exemplary compounds of Formula (I) useful in the present application include, but are not limited to,

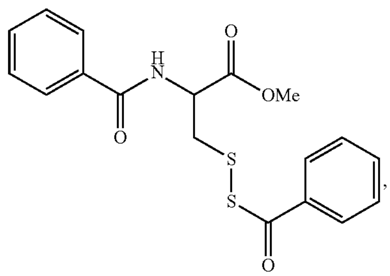

,

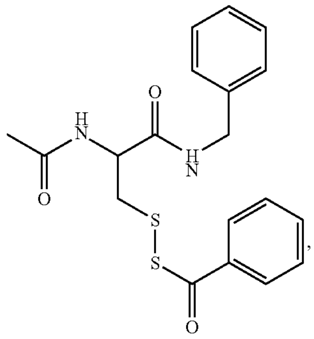

,

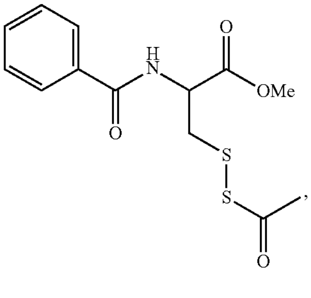

,

-continued

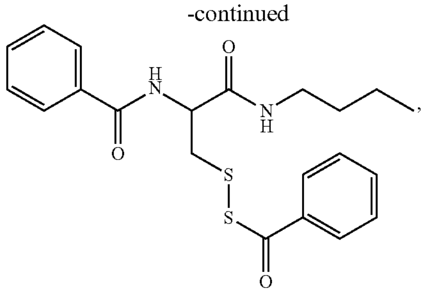

, and

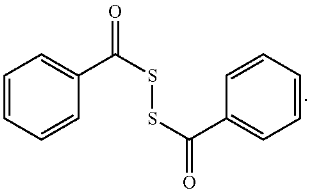

.

The method of vaccinating a subject further includes selecting a subject in need of vaccination against infection by an enveloped virus.

As used herein, a subject includes humans and non-human animals such as non-human primates, dogs, cats, sheep, goats, cows, pigs, horses and rodents.

An "enveloped" virus is an animal virus which possesses a membrane or 'envelope', which is a lipid bilayer containing viral proteins. The envelope proteins of a virus play a pivotal role in its lifecycle. They participate in the assembly of the infectious particle and also play a crucial role in virus entry by binding to a receptor present on the host cell and inducing fusion between the viral envelope and a membrane of the host cell. Enveloped viruses can be either spherical or filamentous (rod-shaped) and include but are not limited to herpesviruses, poxviruses, hepadnaviruses, asfarviridae, flavivirus, alphavirus, togavirus, coronavirus, hepatitis viruses, orthomyxovirus, paramyxovirus, rhabdovirus, bunyavirus, filovirus, and retroviruses.

In one embodiment of the present application, the enveloped virus is selected from the group consisting of Ebola virus, human immunodeficiency virus, influenza virus, Lassa fever virus, Nipah virus, respiratory syncytial virus, Rift Valley fever virus, SARS virus (e.g., SARS-Cov1, SARS-Cov2), MERS virus, Marbury virus, swine pox virus, Cytomegalovirus, Crimean hemorrhagic fever virus, and COVID-19.

The vaccine compositions of the present application can be administered by parenteral, topical, intravenous, oral, subcutaneous, intraperitoneal, intranasal or intramuscular means for prophylactic treatment.

Factors to be accounted for when administering the vaccine of the present application in order to produce a robust immune response, include without limitation the concentrations vaccine, the presence of an adjuvant, the mode and frequency of administration, and the subject details, such as age, weight and overall health and immune condition. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer the vaccine composition until a dosage is reached that provides the desired or required prophylactic effect, e.g., the desired antibody titers. The progress of this therapy can be easily monitored by conventional assays.

In one embodiment of the present application, the vaccine composition as descried herein is administered prophylactically to prevent, delay, or inhibit the development of the infection in a subject at risk being infected with an enveloped virus. In some embodiments of the present application, prophylactic administration of the vaccine composition is effective to fully prevent infection in an individual of the enveloped virus of the vaccine composition. In other embodiments, prophylactic administration is effective to prevent the full extent of infection that would otherwise develop in the absence of such administration, i.e., substantially prevent or inhibit the enveloped virus infection in an individual.

Another aspect of the present application relates to an ex vivo vaccine composition comprising:

one or more isolated enveloped viruses and a compound of the Formula (I):

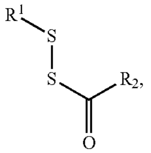

(I)

wherein $R^1$ is

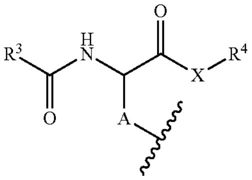

or —C(O)Ph, $R^2$ is $C_{1-6}$ alkyl or aryl;

$R^3$ is $C_{1-6}$ alkyl or aryl;

$R^4$ is $C_{1-6}$ alkyl optionally substituted with aryl;

A is $C_{1-3}$ alkylene;

X is O or NH; and

is the point of attachment of $R^1$ to S, wherein the compound is present in the vaccine composition in an amount sufficient to inactivate said one or more isolated enveloped viruses.

In one embodiment of the ex vivo vaccine compositions of the present application, the composition further includes adjuvants, antibiotics, antivirals, pharmaceutically acceptable carriers, stabilizers, and/or preservatives The vaccine may comprise one or more additional adjuvants which are suitable to initiate or increase an immune response of the innate immune system. Adjuvant generally refers to any material that increases the humoral and/or cellular immune response to an antigen. Traditional vaccines are composed of crude preparation of killed pathogenic microorganisms, and the impurities associated with the cultures of pathological microorganisms could act as adjuvant to enhance the immune response. However, when homogeneous preparations of pathological microorganisms or purified protein subunits are used as antigens for vaccination, the immunity invoked by such antigens is poor and the addition of certain exogenous materials as adjuvants therefore becomes necessary. Further, synthetic and subunit vaccines are expensive to produce. Therefore, with the aid of adjuvants, a smaller dose of antigen may be required to stimulate the immune response, thereby saving the production cost of vaccines.

Adjuvants are known to act in a number of different ways to enhance the immune response. Many adjuvants modify the cytokine network associated with immune response. These immunomodulatory adjuvants can exert their effect even when they are not together with antigens. In general, the immunomodulatory adjuvants cause a general up-regulation of certain cytokines and a concomitant down regulation of others.

Some adjuvants have the ability to preserve the conformational integrity of an antigen so that the antigens can be efficiently presented to appropriate immune effector cells. As a result of this preservation of antigen conformation by the adjuvant formulation, the vaccine would have an increased shelf-life such as that shown for immune stimulating complexes (ISCOMs) (Ozel et. al., Quarternary Structure of the Immunestimmulating Complex (Iscom), J. *of Ultrastruc. and Molec. Struc. Res.* 102: 240-248 (1989), which is hereby incorporated by reference in its entirety).

Some adjuvants have the property of retaining the antigen as a depot at the site of injection. As a result of this depot effect the antigen is not quickly lost by liver clearance. Aluminum salts and the water-in-oil emulsions act through this depot effect for a shorter duration. For example, one can obtain a long-term depot by using Freund's complete adjuvant (FCA) which is a water-in-oil emulsion. FCA typically remains at the injection site until biodegradation permits removal of the antigen by antigen-presenting cells.

Based on their physical nature, adjuvants can be grouped under two very broad categories, namely particulate adjuvants and non-particulate adjuvants. Particulate adjuvants exist as microparticles. The immunogen is either able to incorporate or associate with the microparticles. Aluminum salts, water-in-oil emulsions, oil-in-water emulsions, immune stimulating complexes, liposomes, and nano- and microparticles are examples of particulate adjuvants. The non-particulate adjuvants are generally immunomodulators and they are generally used in conjunction with particulate adjuvants. Muramyl dipeptide (an adjuvant-active component of a peptidoglycan extracted from Mycobacteria), non-ionic block copolymers, Saponins (a complex mixture of triterpenoids extracted from the bark of the *Quillaja saponaria* tree), Lipid A (a disaccharide of glucosamine with two phosphate groups and five or six fatty acid chains generally C12 to C16 in length), cytokines, carbohydrate polymers, derivatized polysaccharides, and bacterial toxins such as cholera toxin and *E. coli* labile toxin (LT) are examples of non-particulate adjuvants.

Some adjuvants are combination of non-particulate immunomodulators and particulate materials which could impart depot effect to the adjuvant formulation. For example, FCA combines the immunomodualtory properties of *Mycobacterium tuberculosis* components along with the short-term depot effect of oil emulsions.

Oil emulsions have been used as vaccine adjuvants for a long time. Le Moignic and Pinoy found in 1916 that a suspension of killed *Salmonella typhimurium* in mineral oil increased the immune response. Subsequently, in 1925, Ramon described starch oil as one of the substances augmenting the antitoxic response to diptheria toxoid. However, the oil emulsions did not become popular until 1937 when Freund came out with his adjuvant formulation now known as Freund's Complete Adjuvant (FCA). FCA is a water-in-oil emulsion composed of mineral (paraffin) oil mixed with killed Mycobacteria and Arlacel A. Arlacel A is principally mannide monooleate and is used as an emulsifying agent. Although FCA is excellent in inducing an antibody response, it causes severe pain, abscess formation, fever and granulomatous inflammation. To avoid these undesirable side reactions, Incomplete Freund's Adjuvant (IFA) was developed. IFA is similar to FCA in its composition except for the absence of mycobacterial components. IFA acts through depot formulation at the site of injection and slow release of the antigen with stimulation of antibody-producing cells.

Exemplary adjuvants that may be useful in the ex vivo vaccine compositions of the present application include, but are not limited, to aluminum salt, inulin, argamline, a combination of inulin and aluminum hydroxide, monophosphoryl lipid A (MPL), resiquimoid, muramyl dipeptide (MDP), N-Glycolyl dipeptide (GMDP, N-glycolyl dipeptide), poly IC, CpG oligonucleotide, resiquimod, aluminum hydroxide containing MPL, a water-in-oil emulsion, squalene or analogs thereof, any pharmaceutically acceptable oil, tween-80, sorbitan trioleate, alpha-tocopherol, cholecalciferol or any analogs thereof, derivatives thereof, calcium-modified forms thereof, phosphate-modified forms thereof, and combinations thereof. Further examples of adjuvants are well known in the art, with some examples being disclosed in U.S. Pat. No. 10,588,956 to Sumathy et al.; U.S. Pat. No. 10,238,736 to Dominowski et al.; U.S. Pat. No. 8,808,710 to Randolph et al.; U.S. Pat. No. 10,143,745 to Vandepapeliere; U.S. Pat. No. 7,378,097 to Glenn et al.; and U.S. Pat. No. 8,858,962 to Tokumoto et al., which are hereby incorporated by reference in their entirety.

Besides the adjuvanticity and safety, the physical appearance of an emulsion is also an important commercial consideration. Physical appearance depends on the stability of the emulsion. Creaming, sedimentation, and coalescence are indicators of the emulsion instability. Creaming occurs when oil and aqueous phases of the emulsion have different specific gravity. Creaming also occurs when the initial droplet size of the emulsion is large and the emulsion droplets are not having any Brownian motion. When the droplet size is large, there is a tendency for the interfacial rupture and the droplets coalesce into large particles. The stability of the emulsion is determined by a number of factors such as the nature and amount of emulsifier used, the size of the droplet size in the emulsion, and the difference in the density between the oil and water phase.

Emulsifiers promote stabilization of dispersed droplets by reducing the interfacial free energy and creating physical or electrostatic barriers to droplet coalescence. Nonionic as well as ionic detergents have been used as emulsifiers. Nonionic emulsifiers orient at the interface and produce relatively bulky structures, which leads to steric avoidance of the dispersed droplets. Anionic or cationic emulsifiers induce formation of an electrical double layer by attracting counter ions; the double layer repulsive forces cause droplets to repel one another when they approach.

The ex vivo vaccine compositions of the present application may further comprise an antibacterial agent. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefbirome, Cefpodoxime, Cefpodoxime-clavulanic acid, Cefpodoxime-sulbactam, Cefbrozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, Voriconazole, and combinations thereof.

The need to add a preservative to vaccines can be reduced or eliminated by making and using only single dose vaccine formulations. However, the use of single-dose preservative-free formulations raises the overall cost of vaccination and threatens the effectiveness of vaccination programs in developing countries. Furthermore, complete removal of preservatives from multidose vials is not considered a preferred option, particularly in countries where cold storage is limited and health care standards are not optimal. Thus, multi-dose vials appear to be most suitable for the manufacture of cheaper vaccines, but formulate multi-dose vaccines with at least one preservative and are used in multiple uses. It is desirable to protect subjects from microorganisms that are inadvertently introduced into the vaccine after a sterility event. However, the efficacy of preservatives in resisting contamination of bacteria and other microorganisms is specific for the immunogenicity and long-term stability of each different antigenic determinant in an optimal immunogenic composition.

Possible preservatives approved for use in injectable drugs which may be compatible with the vaccine formulations of the present application include but are not necessarily limited to chlorobutanol, m-cresol, methylparaben, propylparaben, 2-phenoxyethanol, benzethonium chloride, benzalkonium chloride, benzoic acid, benzyl alcohol, phenol, thimerosal, phenylmercuric nitrate, and combinations thereof.

The ex vivo vaccine compositions of the present application may be formulated for parenteral administration. Solutions, suspensions, or emulsions of the composition can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical vaccine formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

One or more compatible solid or liquid fillers or diluents or encapsulating compounds, which are suitable for administration to a patient to be treated, may be used as well for the vaccine according to the present application. The term "compatible" as used here means that these constituents of the combination vaccine are capable of being mixed with the components of the combination vaccine in such a manner that no interaction occurs which would substantially reduce the pharmaceutical effectiveness of the combination vaccine under typical use conditions.

As used herein, the term "pharmaceutical acceptable carrier" means a non-toxic, inert solid, semi-solid or liquid filler, diluent, encapsulating material, or formulation auxiliary of any type. Such a pharmaceutically acceptable carrier typically includes the liquid or non-liquid basis of a composition comprising the components of the combination vaccine. If the composition is provided in liquid form, the carrier will typically be pyrogen-free water; isotonic saline or buffered (aqueous) solutions (e.g. phosphate, citrate, etc.) buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. For example, Ringer-Lactate solution is a commonly used carrier.

The ex vivo vaccine compositions of the present application may contain stabilizers. In general, stabilizers are added to vaccine formulations to help maintain the vaccines effectiveness. The stability of the vaccine is critical as instability can lead to the loss of the antigenic effect of the vaccine. Exemplary stabilizers include, but are not limited to, sorbitol, L-glycine, mannitol, L-glutamic acid, human serum albumin, and combinations thereof.

Optionally, the ex vivo vaccine composition of the present application can further include an antiviral agent. Exemplary antiviral agents that may be used in the present application include, but are not limited to nucleoside analogs (e.g., zidovudine, acyclovir, gancyclovir, vidarabine, idoxuridine, trifluridine, and ribavirin), foscarnet, amantadine, peramivir, rimantadine, saquinavir, indinavir, ritonavir, alpha-interferons and other interferons, AZT, t-705, zanamivir (Relenza®), and oseltamivir (Tamiflu®). Other anti-viral agents include influenza virus vaccines, e.g., Fluarix® (Glaxo SmithKline), FluMist® (Medlmmune Vaccines), Fluvirin® (Chiron Corporation), Flulaval® (GlaxoSmithKline), Afluria® (CSL Biotherapies Inc.), Agriflu® (Novartis), Fluzone® (Aventis Pasteur), and combinations thereof.

Preferences and options for a given aspect, feature, embodiment, or parameter of the technology described herein should, unless the context indicates otherwise, be regarded as having been disclosed in combination with any and all preferences and options for all other aspects, features, embodiments, and parameters of the technology.

The following Examples are presented to illustrate various aspects of the present application, but are not intended to limit the scope of the claimed application.

EXAMPLES

The examples below are intended to exemplify the practice of embodiments of the disclosure but are by no means intended to limit the scope thereof.

Materials and Methods

Small-Molecule Compounds Tested

XM-01 and other sulfur-containing compounds tested (FIG. 1A) were used in previous studies as $H_2S$ donors. These compounds were synthesized using known protocols (Zhao et al., "Controllable Hydrogen Sulfide Donors and Their Activity Against Myocardial Ischemia-Reperfusion Injury," *ACS Chem. Biol.* 8:1283-1290 (2013), which is hereby incorporated by reference in its entirety). All stock solutions for these compounds were prepared in 100% DMSO, stored at −20° C., and used within 6 months of reconstitution

LJ001

The control compound LJ001 was synthesized at the University of California, Los Angeles (UCLA) by Dr. Michael Jung's group (Wolf et al., "A Broad-spectrum Antiviral Targeting Entry of Enveloped Viruses," PNAS 107:3157-3162 (2010), which is hereby incorporated by reference in its entirety. LJ001 was reconstituted in 100% DMSO, protected from light, stored at −20° C., and used within 6 months of reconstitution.

Cell Culture

HEK293T (ATCC) and PK13 cells (ATCC) were cultured in Dulbecco's modified Eagle's medium with 10% fetal bovine serum (FBS) (Gibco, Life Technologies). Vero cells (ATCC) were cultured in minimal essential medium alpha with 10% FBS. Human lung epithelial cells (A549, ATCC), and Madin-Darby canine kidney epithelial cells (MDCK, ATCC) were grown in complete DMEM containing 10% FBS, 100 IU/mL penicillin, 100 μg/mL streptomycin (Gibco, Life Technologies). MA104 cells were obtained from ATCC and grown in Dulbecco's modified Eagle's medium with 10% FBS, 100 IU/mL penicillin, 100 μg/mL streptomycin.

Cytotoxicity Assay

Vero cells (ATCC) were incubated with each compound for 30 min to 24 h, as indicated, at the specified concentrations. This was followed by incubation with a cell counting kit reagent (CKK-8) (Dojindo Molecular Technologies, Japan) for 1-2 hour, absorbance was measured at 450 nm using an infinite M100 microplate reader (Tecan Ltd). The quantity of the formazan dye produced when WST-8 (Dojindo) is reduced by dehydrogenases is directly proportional to the number of living cells (i.e. cell viability) (Tominaga et al., "A Water-soluble Tetrazolium Salt Useful for Colorimetric Cell Viability Assay," *Anal. Commun.* 36:47-50 (1999), which is hereby incorporated by reference in its entirety).

Cell-Cell Fusion Quantification

HEK293T cells grown in 6-well plates were transfected at 70-90% confluency with NiV F and G DNA expression plasmids (1:1 ratio, 2 μg total DNA per well) using Lipofectamine 2000 (Invitrogen). 18 h post-transfection cells were fixed in 0.5% paraformaldehyde (PFA) and syncytia were counted under an inverted microscope (200×). A syncytium was defined as four or more nuclei within a single cell. Five fields per well were counted for each experiment.

Receptor EphrinB2 and Antibody Binding Measured by Flow Cytometry

For receptor binding, HEK293T cells were transfected with 2 μg NiV G expression plasmids and collected 24 h post-transfection. Collected cells were then incubated with compound for 30 min followed by incubation with soluble ephrinB2 (R&D systems, MN) at 100 nM for 1 hour. This was followed by two washes with FACS buffer (1% heat-inactivated FBS in PBS) and incubation with anti-human Alexa Fluor 647 fluorescent antibody (Life Technologies, NY) diluted 1:200 for 30 min at 4° C., followed by two washes. Cells were fixed in 0.5% PFA and read on a flow cytometer (Guava easyCyte8 HT, EMD Millipore, MA).

Transmission Electron Microscopy (TEM) Imaging

5 μL of VLPs or VSV-NiV suspension (prepared as previously described) were pipetted onto a 200-mesh Formvar-coated nickel grid and allowed to settle for 20 min at room temperature. Excess liquid was removed by wicking with filter paper before coating the deposited sample with 5 μL of 1% uranyl acetate (UA) (Polysciences, Inc). After 2.5 min, excess UA was wicked off using filter paper and dried overnight in a desiccator. TEM micrographs of the samples were recorded under a high vacuum with an electron beam strength set at 200 kV using the FEI Technai G2 20 Twin TEM (FEI Corp., Hillsboro, OR).

Testing XM-01 Effects on Triggering of NiV-F

F-triggering assays were performed essentially as previously described ((Aguilar et al., "A Quantitative and Kinetic Fusion Protein-Triggering Assay Can Discern Distinct Steps in the Nipah Virus Membrane Fusion Cascade," *J. Virol.* 84:8033-8041 (2010), which is hereby incorporated by reference in its entirety) with some optimizations. PK13 cells were transfected with NiV F expressing in a pCAGGS plasmid, NiV G expressing in a pcDNA3.1$^+$ plasmid, and green fluorescent protein (GFP) expressing in a pMAX plasmid at a 13:6:1 ratio, respectively. At 24 h post-transfection, cells were mixed with untransfected PK13 (negative control) or PK13-B2 (receptor-expressing) cells at a 1:1 ratio and incubated for 60 min at 4° C. or 37° C. in the presence of HR2-Cy5 peptide (Cy5 fluorophore purchased from Lumiprobe) (Cy5-KVDISSQIS-SMNQSLQQSKDYIKEAQRLLDTVNPSL (SEQ ID NO: 1)) and 1 μM of DMSO (vehicle control) or XM-01. Subsequently, cells were brought out of solution and resuspended in FACS buffer. HR2-Cy5 peptide bound to triggered NiV-F was detected with the Cy5 fluorophore by flow cytometric analysis, using a Guava easyCyte8HT flow cytometer (EMD Millipore, MA); data were normalized to wildtype mean fluorescence intensity (MFI).

RNA Stability Assay

Briefly, 20 μg of an nsp3: luciferase construct was either treated with 1, 3, 10, 30, 10 μM concentrations of XM-01 for 1 h on ice. These mixtures were then electroporated into untreated BHK cells. BHK cells pretreated with XM-01, cells were incubated with DMSO or 100 μM treatment of XM-01 for 45 min followed by electroporation of 20 μg of RNA. A positive control was also performed, consisting of 20 μg RNA treated with RppH for 1.25 h at 37° C. followed by enzyme inactivation at 65° C. for 10 min. The decapped samples were then mixed with 100 μM of XM-01 on ice for 1 h before being electroporated into BHK cells.

Pseudotyped Virus Production

Pseudotyped virions containing NiV F and NiV G were manufactured as previously described (Aguilar et al., "N-glycans on Nipah Virus Fusion Protein Protect Against Neutralization but Reduce Membrane Fusion and Viral Entry," *J. Virol.* 80:4878-4889 (2006), which is hereby incorporated by reference in its entirety). Briefly, 15 cm plates of 293T cells were transfected at 37° C. with NiV-F and NiV-G expression plasmids at a 1:1 ratio. 8 h post-transfection, the media was switched to fresh growth media. After an additional 16 h the cells were infected with recombinant VSV-AG-rLuc. 2 h later the infection media was removed and replaced with growth media. 24 h after infection virions were harvested from cell supernatants using ultracentrifugation, re-suspended in NTE buffer with 5% sucrose, and stored at −80° C. in 100 μL aliquots.

Detection of Protein Conformations by Flow Virometry

Pseudotyped NiV (pNiV) virions were incubated for 30 min with XM-01 at 4° C., then washed by ultracentrifugation with NTE buffer (150 mM NaCl, 40 mM Tris-HCl at pH 7.5, and 1 mM EDTA) at 35,000 rpm for 2 hours. The treated virus was re-suspended in NTE buffer, then stained as previously described (Landowski et al., "Nipah Virion Entry Kinetics, Composition, and Conformational Changes Determined by Enzymatic Virus-Like Particles and New Flow Virometry Tools," *J. Virol.* 88:14197-14206 (2014), which is hereby incorporated by reference in its entirety). Anti-NiV F and/or anti-NiV G specific rabbit 1° antibodies (Anti NiV F Ab 66, or anti-NiV G Ab 213) (Aguilar et al., "Polybasic KKR Motif in the Cytoplasmic Tail of Nipah Virus Fusion Protein Modulates Membrane Fusion by Inside-Out Signaling," *J. Virol.* 81:4520-4532 (2007); Aguilar et al., "A Novel Receptor-induced Activation Site in the Nipah Virus Attachment Glycoprotein (G) Involved in Triggering the Fusion Glycoprotein (F)," *J. Biol. Chem.* 284:1628-1635 (2009); Liu et al., "Nipah Virus Attachment Glycoprotein Stalk C-Terminal Region Links Receptor Binding to Fusion Triggering," *J. Vorol.* 89:1838-1850 (2015), which are hereby incorporated by reference in their entirety) were used at a 1:100 dilution for 1 h followed by a FACS buffer (1% FBS in PBS) wash and incubation with 2° antibody Alexa 647 goat and anti-rabbit (Life Technologies, NY) for 30 min followed by one more FACS buffer wash. Then, the relative levels of antibody binding were measured by the recently developed flow virometry technique, using a Guava easyCyte8HT flow cytometer (EMD Millipore, MA) (Landowski et al., "Nipah Virion Entry Kinetics, Composition, and Conformational Changes Determined by Enzymatic Virus-Like Particles and New Flow Virometry Tools," *J. Virol.* 88:14197-14206 (2014), which is hereby incorporated by reference in its entirety). Background mean fluorescence intensity (MFI) obtained by binding equal concentrations of primary and secondary reagents to mock virus obtained by transfecting HEK293T cells with the PCDNA3.1$^+$ backbone DNA expression vector were then subtracted from the MFI of pseudotyped NiV/VSV virions.

Pseudotyped NiV/VSV Viral Infection Assays

Virus particles were incubated for 30 min with or without the indicated amounts of the compound or the corresponding vehicle DMSO control. Then, Vero cells were infected with 10-fold dilutions of pseudotyped virus particles in infection buffer (PBS+1% FBS) and incubated for 2 hours at 37° C. After 2 h, growth medium was added. 18-24 h post-infection cells were lysed and an infinite M1000 microplate reader (Tecan Ltd) was used to measure luciferase activity.

Plaque Assay for Measurement of HSV-1 Infections

XM-01 was incubated for 30 min with HSV-1 KOS (100 PFU/well) and then the mix was added to Vero cells. At 3 h post-inoculation, the medium was removed. At 18 to 24 h post-infection, the culture medium was removed, and cells were fixed with an ice-cold methanol-acetone solution (2:1 ratio) for 20 min at 20° C. and air-dried. Virus titers were determined by immunoperoxidase staining with anti-HSV polyclonal antibody HR50 (Fitzgerald Industries, Concord, MA) (Roller et al., "Structure-Function Analysis of Herpes Simplex Virus Glycoprotein B with Fusion-from-without Activity," Virology 382:207-216 (2008), which is hereby incorporated by reference in its entirety).

Plaque Assay for Measurement of RSV Infections

Human respiratory syncytial virus (RSV A2 strain) was propagated on CV 1 cells (ATCC) and purified by centrifuging two times on discontinuous sucrose gradients as described previously (Tsai et al., "DAMP Molecule S100A9 Acts as a Molecular Pattern to Enhance Inflammation During Influenza A Virus Infection: Role of DDX21-TRIF-TLR4-MyD88 Pathway," *Plos Pathog.* 10 (1):e1003848 (2014); Tsai et al., "Regulation of TLR3 Activation by S100A9," *J. Immunol.* 195:4426-4437 (2015), which are hereby incorporated by reference in their entirety). XM-01 (10 or 30 μM as indicated) was incubated with purified RSV at room temperature for 45 min or 2 h before infecting A549 cells at a multiplicity of infection (MOI) of 0.5 or 0.01. Briefly, the XM-01 pre-treated RSV was adsorbed onto the cells in serum-free, antibiotic-free OPTI-MEM medium (Gibco) for 1.5 h at 37° C. Following adsorption, A549 cells were washed with PBS and the infection was continued for 16 h in the presence of XM-01 before collecting the supernatant. A plaque assay was performed to determine the viral titer (pfu/mL) in the collected supernatant. Briefly, CV-1 cells were infected with serial dilutions of the culture supernatant in a 12-well plate as described above. After 1.5 h, the cells were washed with PBS and the medium was replaced with 1% methylcellulose in the complete growth medium. Plaques were stained after 24-48 h with 1% crystal violet and counted to determine the viral titer.

Plaque Assay for Measurement of A/WSN/33 and Ca/04/2009 H1N1 Influenza Virus Infections The A/WSN/33 strain of the influenza virus was serially diluted and then treated with either DMSO, 30 μM XM-01, or 1 μM LJ001 for 30 min at 4° C., Ca/04/09 H1N1 was inactivated for 4 h at room temperature. Treated dilutions of the virus were titrated on MDCK cells by standard plaque assay and plaque-forming units were stained with crystal violet and counted 3-5 days post-infection (Goodman et al., "The Alpha/Beta Interferon Receptor Provides Protection Against Influenza Virus Replication but is Dispensable for Inflammatory Response Signaling," *J. Virol.* 84:2027-2037 (2010), which is hereby incorporated by reference in its entirety).

Rotavirus Infection Assays

18β-glycyrrhetinic acid (GRA) (Sigma-Aldrich) stock solutions were prepared to a concentration of 100 mg/mL in DMSO and aliquots were stored at −80° C. The stock solutions were diluted to working concentrations in DMEM without FBS. For the control compounds, MA104 (ATCC) cells were treated for 6 h with 25 μg/mL GRA. The viability was measured with the Promega CellTiterGlo Assay according to the manufacturer's protocol, with digitonin as the control for 100% cytotoxicity. Data shown are representative of two experiments, with each concentration tested in triplicate in each experiment. Error bars indicate SEM. To test XM-01, after MA104 cells were infected with $8.9\times10^5$ pfu/well of trypsin-activated bovine rotavirus strain NCDV. Mock-infected wells received 50 μl of 0% M199 vehicle media. 50 μl of fresh 2× control and experimental compounds were added and at 18 h post-infection, the cells were fixed for 10 min with 80% acetone (Hardy et al., "18 Beta-glycyrrhetinic Acid Inhibits Rotavirus Replication in Culture," *Virol. J.* 9:96 (2012), which is hereby incorporated by reference in its entirety).

Plaque Assay for Measurement of Norovirus Infection

RAW 264.7 (ATCC) cells were infected with serial dilutions of norovirus for 1 h. 3% wt/vol Seaplaque agarose in 2×MEM media was placed as a first overlay. Then, cells were incubated for 48 h when plaques were visible and counted.

Lipids and Peptides

Lipids POPC, POPS, and the chain spin-labeled 5PC, 16PC and a head group spin-label dipalmitoylphospatidyl-tempo-choline (DPPTC) were purchased from Avanti Polar Lipids (Alabaster, AL) cholesterol was purchased from Sigma (St. Louis, MO) and used without further modification.

Electron Spin Resonance

Prepared MLVs (POPC, POPG and 0.5% (mol:mol) spin-labeled lipids), were resuspended and hydrated in the buffer (5 mM HEPES, 10 mM IVIES, 150 mM NaCl, pH 7) at room temperature for 2 h. Varying amounts of XM-01 (1 mg/mL in DMSO) were added to the MLV dispersion for 1 h incubation at room temperature, along with the vehicle control. The mixture was then pelleted and transferred to a quartz capillary tube for ESR measurement. ESR spectra were collected on an ELEXSYS ESR spectrometer (Bruker Instruments, Billerica, MA) at X-band (9.5 GHz) using an N2 Temperature Controller (Bruker Instruments, Billerica, MA).

The ESR spectra were analyzed using the NLLS fitting program based on the stochastic Liouville equation (Budil et al., "Nonlinear-least-squares Analysis of Slow-motion EPR Spectra in One and Two Dimensions Using a Modified Levenberg-Marquardt Algorithm," *J. Magn. Reson.* 120:155-189 (1996); Liang and Freed, "An Assessment of the Applicability of Multifrequency ESR to Study the Complex Dynamics of Biomolecules," *J. Phys. Chem. B* 103:6384-6396 (1999), which are hereby incorporated by reference in their entirety) using the MOMD or Microscopic Order Macroscopic Disorder model as in previous studies (Ge and Freed, "Fusion Peptide from Influenza Hemagglutinin Increases Membrane Surface Order: An Electron-Spin Resonance Study," *Biophys. J.* 96:4925-4934 (2009); Lai and Freed, "HIV gp41 Fusion Peptide Increases Membrane Ordering in a Cholesterol-Dependent Fashion," *Biophys. J.* 106:172-181 (2014); Lai and Freed, "The Interaction Between Influenza HA Fusion Peptide and Transmembrane Domain Affects Membrane Structure," *Biophys. J.* 109:2523-2536 (2015); Pinello et al., "Structure-function Studies Link Class II Viral Fusogens with the Ancestral Gamete Fusion Protein HAP2," *Curr. Biol.* 27:651-660 (2017); Ge and Freed, "Two Conserved Residues Are Important for Inducing Highly Ordered Membrane Domains by the Transmembrane Domain of Influenza Hemagglutinin," *Biophys. J.* 100:90-97 (2011), which are hereby incorporated by reference in their entirety). Each experiment (and subsequent fit) was repeated 2 or 3 times to check reproducibility and estimate experimental uncertainty XM-01 Decomposition Mechanism.

To a solution of XM-01 (50 mg, 0.13 mmol) in $CH_2Cl_2$ (10 mL) was added butyl amine (47.4 mg, 0.65 mmol). The reaction mixture was allowed to stir under room temperature for 2 h. The mixture was then concentrated and subjected to column chromatography (30% Ethyl acetate/Hexane) to separate the products (33 mg) as a mixture of disulfide and polysulfides. The formation of these products indicates the presence of the persulfide intermediate (RSSH) from XM-01.

Disulfide: $^1H$ NMR (300 MHz, Chloroform-d) δ 7.88-7.75 (m, 4H), 7.59-7.49 (m, 2H), 7.47-7.34 (m, 4H), 7.11 (d, J=7.3 Hz, 2H), 5.07 (dt, J=7.3, 5.1 Hz, 2H), 3.78 (s, 6H), 3.35 (d, J=5.1 Hz, 4H); HRMS (ESI) m/z calcd for C22H25N2O6S2 $[M+H]^+$ 477.1154, found 477.1148.

Polysulfides: $^1H$ NMR (300 MHz, Chloroform-d) δ 7.95-7.70 (m, 4H), 7.60-7.33 (m, 6H), 7.24-7.02 (m, 2H), 5.19-4.95 (m, 2H), 3.89-3.69 (m, 6H), 3.65-3.42 (m, 2H); HRMS (ESI) m/z calcd for trisulfide $C_{22}H_{25}N_2O_6S_3$ $[M+H]^+$ 509.0875, found 509.0868; tetrasulfide $C_{22}H_{25}N_2O_6S_4$ $[M+H]^+$541.0595, found 541.0587; pentasulfide $C_{22}H_{25}N_2O_6S_5$ $[M+H]^+$ 573.0326, found 573.0313; hexasulfide $C_{22}H_{25}N_2O_6S_6$ $[M+H]^+$ 605.0037, found 605.0053.

Vaccine Generation.

A/California/04/2009 was thawed on ice before being incubated for 4 h at room temperature with a saturated solution (1 mM) of XM-01 1% DMSO, 10 μM JL-122, 0.02% formalin, and a mock control with vehicle only (1% DMSO) the solutions were then mixed 1:1 with alum before 100 μL was injected intramuscularly to mice.

Hemagglutination Inhibition Assay

To a V-bottom 96-well plate, serum samples in HI buffer were added and diluted by 2-fold serial dilutions then 10 HA units of Ca/04/2009 H1N1 in HI buffer was added. The plate was incubated at room temperature for 30-45 min followed by the addition of 0.8% rooster blood in HI buffer. Results were read 45 min later.

Neuraminidase Inhibition Assay

Neuraminidase inhibition assays were performed using a protocol adapted from Leang and Hurt (Leang and Hurt, "Fluorescence-based Neuraminidase Inhibition Assay to Assess the Susceptibility of Influenza Viruses to The Neuraminidase Inhibitor Class of Antivirals," *Jove-J Vis. Exp.* (122):55570 (2017), which is hereby incorporated by reference in its entirety). In short, sera taken from mice was diluted using 2 fold dilutions and incubated with Ca/04/2009 H1N1 virus in flat-bottom plates in a 1× stock buffer for 30-45 min at room temperature before the addition of the MUNANA substrate. The plate was incubated covered at 37° C. for 1 h before the addition of the stop solution. Results were read using a Tecan Spark plate reader set to 355 nm excitation measuring absorbance at 460 nm.

Animal Care

Vaccination studies were performed in the biosafety level 2 facilities at the Cornell University College of Veterinary Medicine. All works were operated under protocols approved by the CARE and the Cornell University IACUC policies.

Example 1—XM Compounds Inhibit Pseudotyped NiV Infection

Figure 1B:
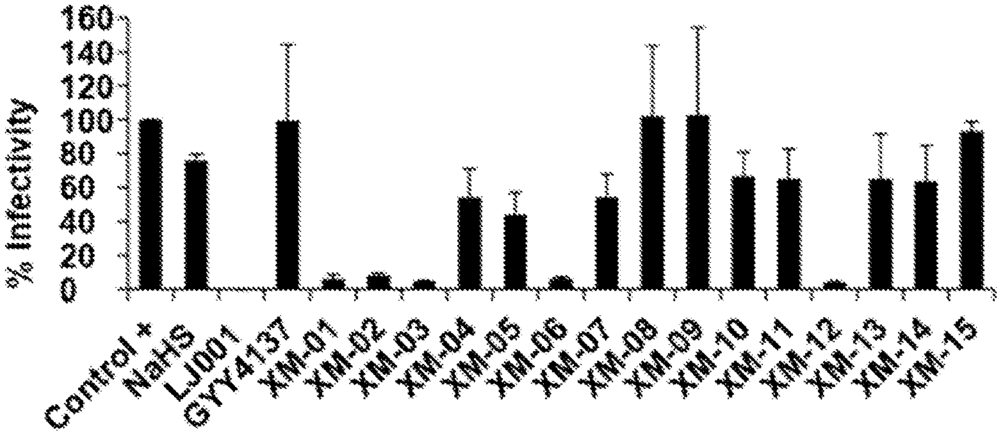

A library of sulfur-containing compounds were screened, comparing them with known hydrogen sulfide donors NaHS and GYY4137 (Li et al., "Role of Hydrogen Sulfide in Paramyxovirus Infections," *J. Virol.* 89:5557-5568 (2015); Zhao et al., "Controllable Hydrogen Sulfide Donors and Their Activity Against Myocardial Ischemia-Reperfusion Injury," *ACS Chem. Biol.* 8:1283-1290 (2013); Li et al., "Characterization of a Novel, Water-Soluble Hydrogen Sulfide-Releasing Molecule (GYY4137): New insights into the Biology of Hydrogen Sulfide," *Circulation* 117:2351-2360 (2008), which are hereby incorporated by reference in their entirety). Also included was LJ001, an inhibitor of virus entry. Representative compounds are depicted in FIG. 1A (Vigant et al., "A Mechanistic Paradigm for Broad-Spectrum Antivirals that Target Virus-Cell Fusion," *Plos Pathog.* 9(4):e1003297 (2013), which is hereby incorporated by reference in its entirety). These compounds were tested as antiviral inhibitors using the well-established high-throughput pseudotyped NiV/VSV virus (pNiV) luciferase infection system (Aguilar et al., "N-glycans on Nipah Virus Fusion Protein Protect Against Neutralization but Reduce Membrane Fusion and Viral Entry," *J. Virol.* 80:4878-4889 (2006); Aguilar et al., "Polybasic KKR Motif in the Cytoplasmic Tail of Nipah Virus Fusion Protein Modulates Membrane Fusion by Inside-Out Signaling," *J. Virol.* 81:4520-4532 (2007), which are hereby incorporated by reference in their entirety). Pretreatment of pNiV with their respective compounds before infection showed a significant decrease in infectivity. Interestingly, the five compounds (XM-01, -02, -03, -06, and -12) that best inhibited pNiV infections all contained acyl disulfide moieties (FIG. 1B).

Figure 1C:
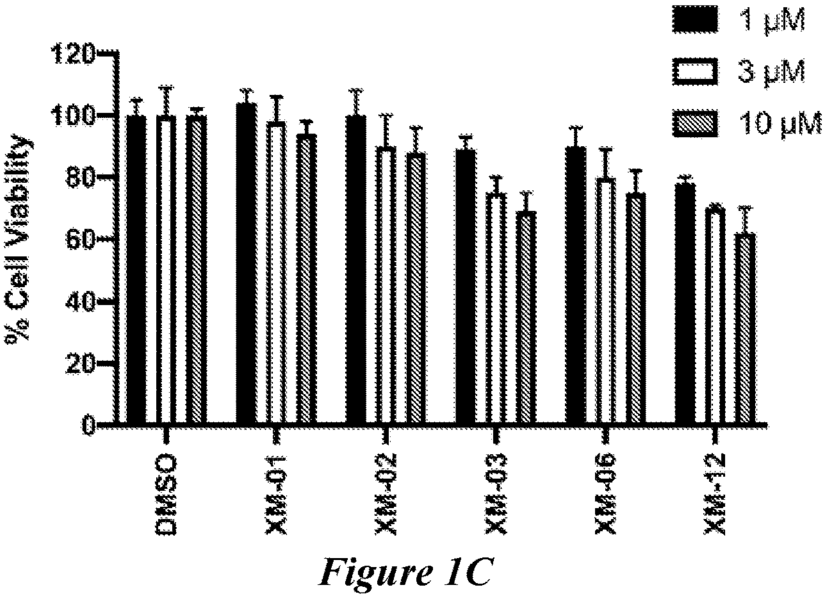

Then, these compounds were tested for cytotoxicity effects using a CCK8 cytotoxicity kit that measures dehydrogenase enzymatic activity (Tominaga et al., "A Water-soluble Tetrazolium Salt Useful for Colorimetric Cell Viability Assay," *Anal. Commun.* 36:47-50 (1999), which is hereby incorporated by reference in its entirety). XM-01 was selected for further characterization as it showed high infectivity inhibitory properties at 10 μM (FIG. 1B) and little to no cytotoxicity at 1-10 μM concentrations (FIG. 1C). The cytotoxic effects of XM-01 were then tested at concentrations between 1-1 mM in Vero cells and 1-100 μM in MDCK cells (Haviernik et al., "Arbidol (Umifenovir): A Broad-Spectrum Antiviral Drug That Inhibits Medically Important Arthropod-Borne Flaviviruses," *Viruses* 10(4):184 (2018), which is hereby incorporated by reference in its entirety). $H_2O_2$ at a 2 mM concentration was used as a cytotoxicity control and the DMSO vehicle control was 0.1 mM for all treatments (FIGS. 2A and 2B).

Example 2—XM-01 Inhibits Enveloped Viruses but not Non-Enveloped Viruses

Figure 2A:
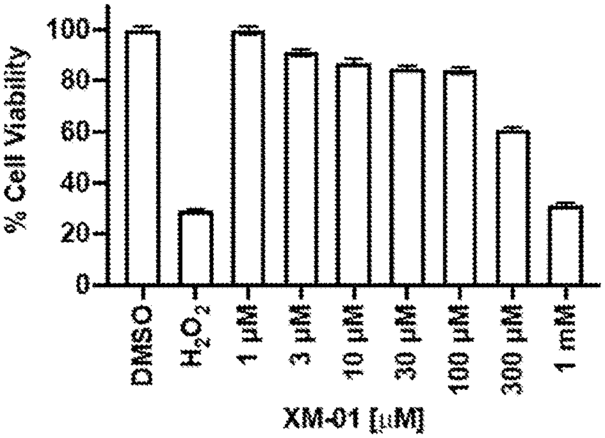
FIGS. 2A-2E depict that XM-01 inhibits enveloped viruses, but not non-enveloped viruses. The percent cell viability was determined using a CCK-8 kit to measure the dehydrogenase activity of cells. Graphical representations of XM-01 cytotoxicity in Vero and in MDCK cells are shown in FIGS. 2A and 2B, respectively. XM-01 cytotoxicity was tested at concentrations between 1 μM-1 mM. DMSO vehicle control=0.1%. Cytotoxic control=2 mM. (N=3).
Figure 2B:
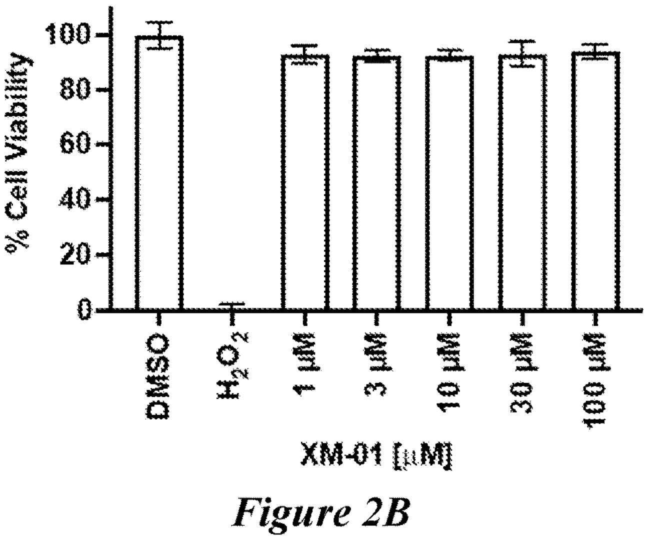
Figure 2C:
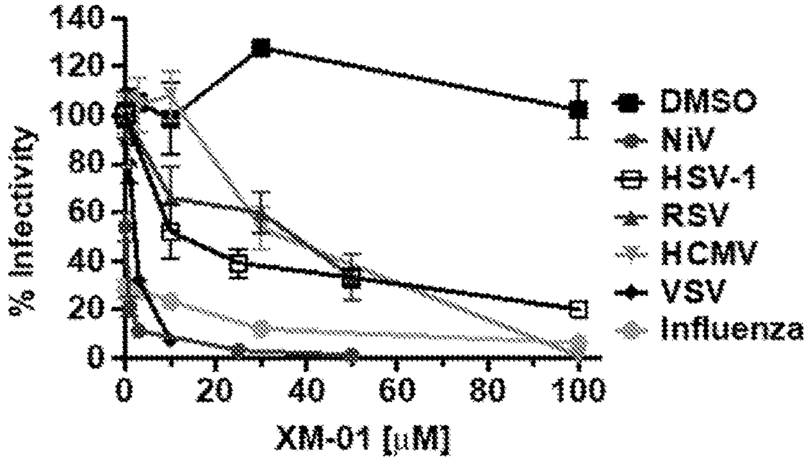
Figure 2D:
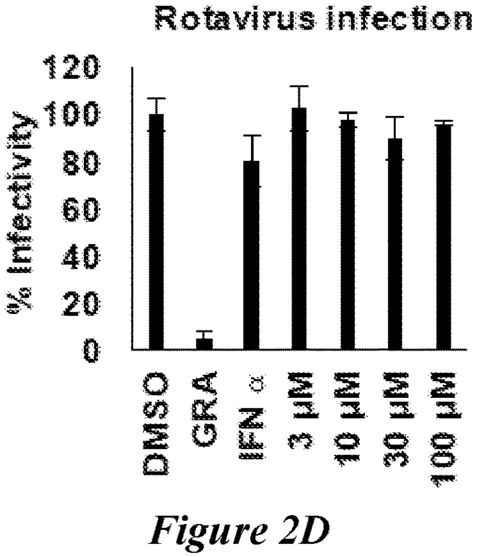
Figure 2E:
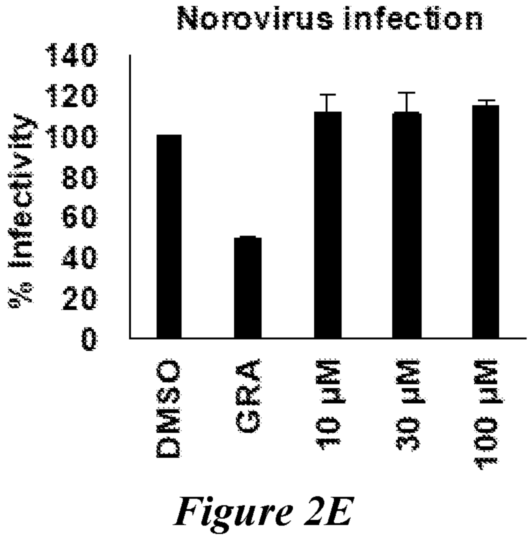

It was observed that not only pNiV, but also the DNA viruses HSV-1 and Human Cytomegalovirus (HCMV), and the RNA viruses respiratory syncytial virus (RSV), vesicular stomatitis virus (VSV), and influenza A/California/04/2009 viruses were inhibited by XM-01 in a concentration-dependent fashion (FIG. 2A). For example, for pNiV, XM-01 was effective at a low micromolar inhibitory concentration $EC_{50}$~1 μM and had a ~3-log difference between the inhibitory and cytotoxic concentrations $CC_{50}$~1 mM, yielding a selectivity index of 1,000, which is typically acceptable for therapeutic purposes (FIGS. 1C and 2A). In contrast, entry of the non-enveloped rotavirus (FIG. 2D) or norovirus (FIG. 2E) was not inhibited. Collectively, these results indicate that XM-01 inhibits enveloped viruses regardless of their DNA or RNA content, but not non-enveloped viruses, suggesting that viral membranes are the primary target.

Figure 3A:
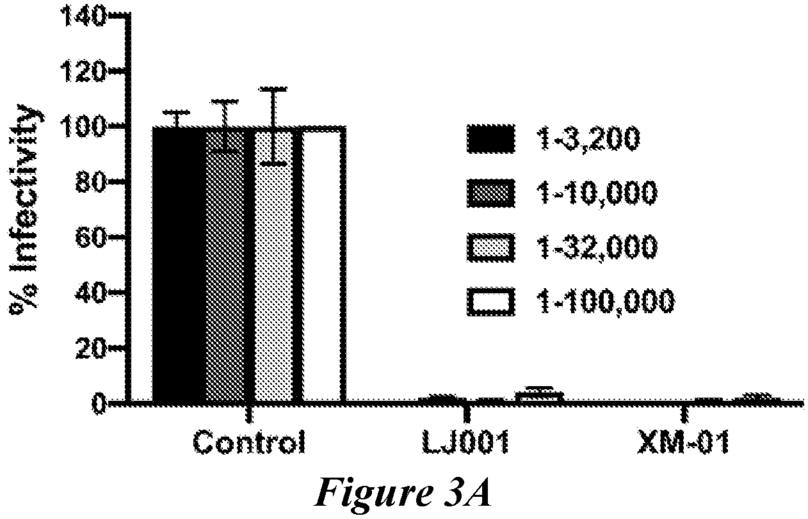
FIGS. 3A-3D depict that XM-01 inhibits virions directly.

Example 3—XM-01 Inhibits Virions Directly, Early in the Infection Process, and in the Absence of Light To begin to elucidate the mechanism of action, XM-01 was tested to determine if it inhibited infections by acting directly on the virions or the cells. First, pNiV were incubated with XM-01 for 30 min and then washed by ultracentrifugation with PBS to remove unbound XM-01. Cells were then infected with the serially diluted virus. The XM-01 treated virions were highly inhibited in their capability to infect Vero cells as compared to the vehicle-treated virus, indicating that XM-01 acts directly on the virus, and not the cells (FIG. 3A).

Figure 3B:
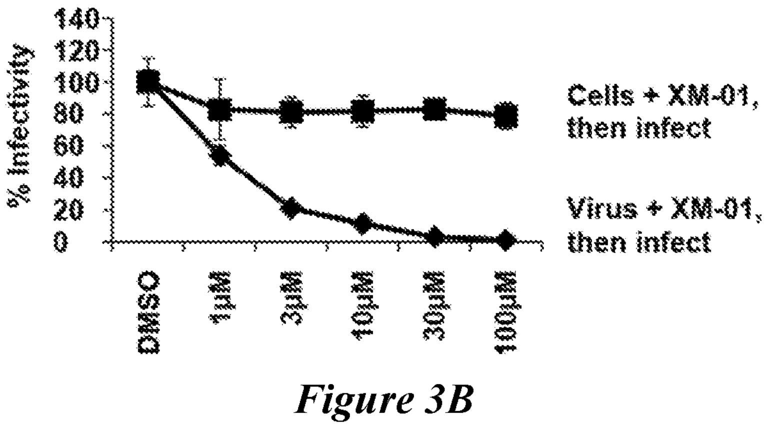

To corroborate this result, cells were pretreated with XM-01 for 30 min and washed away XM-01 using PBS, before infecting the cells with untreated virions. In contrast to the effects of XM-01 on virions in FIGS. 3A and 3B, the compound did not significantly reduce viral infection (FIG. 3B). These experiments further indicate that the effects of XM-01 are directly on the virions.

Figure 3C:
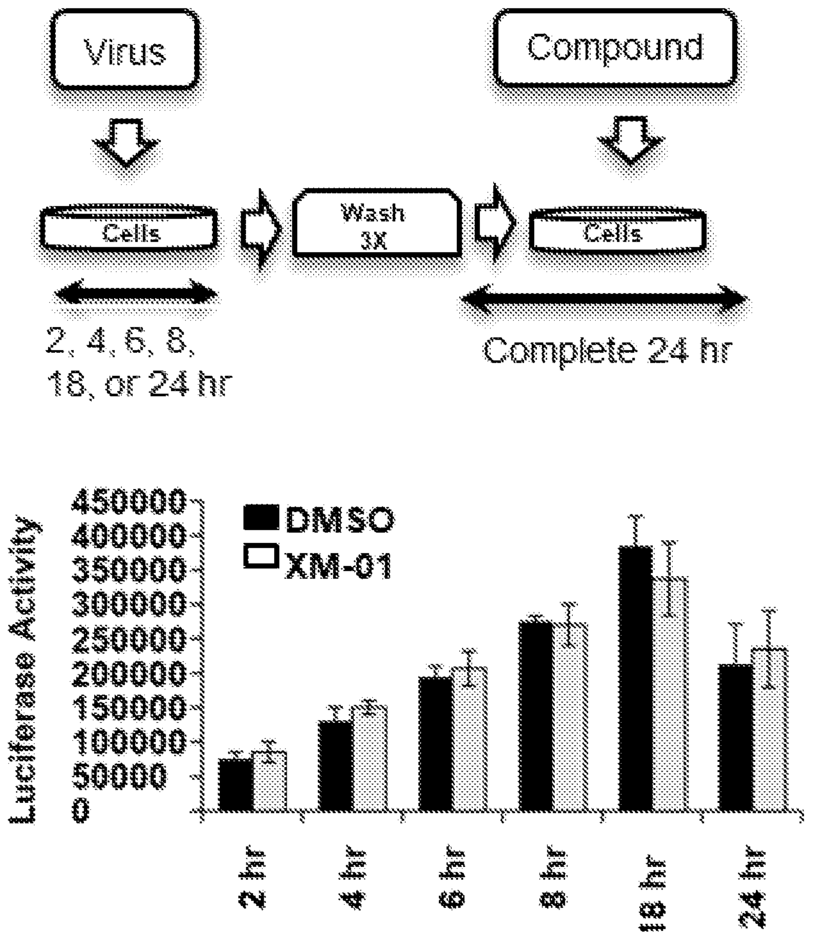

Next, it was sought to determine if XM-01 inhibits viral infection post-entry. A "time of XM-01 addition" experiment was performed wherein XM-01 was added to cells at different time points (FIG. 3C). Vero cells were infected for 2, 4, 6, 8, 18, or 24 h. After infection, the unbound virus was washed from the cells, followed by the addition of XM-01 in media and incubated for additional time necessary to complete a 24 h period. Infection was measured by luciferase activity (FIG. 3C). Two conclusions could be reached. First, as expected, the longer the virus was in contact with cells, the higher the level of infection observed. Second, after any given length of time of infection, XM-01 was completely incapable of inhibiting the infection, as compared to the respective DMSO vehicle control. This indicates that once the virus has entered the cells, XM-01 does not exert inhibitory activity or cytotoxicity, consistent with XM-01 inhibiting a viral entry step (FIG. 3C).

Figure 3D:
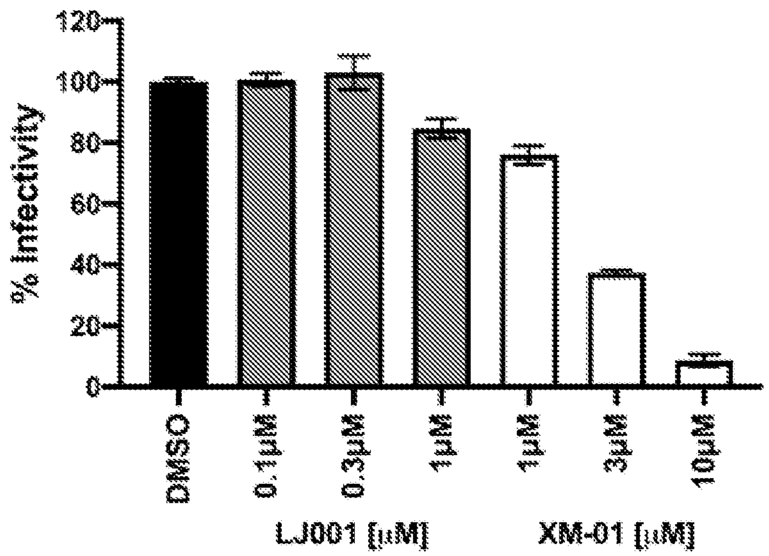

Additionally, XM-01 was tested to determine whether it requires light for activation, as LJ001 and related compounds depend on photons of specific wavelengths to generate radicals (Balmer et al., "Inhibition of an Aquatic Rhabdovirus Demonstrates Promise of a Broad-Spectrum Antiviral for Use in Aquaculture," *J. Virol.* 91(4): e02181 (2017); Balmer et al., "Broad-Spectrum Antiviral JL122 Blocks Infection and Inhibits Transmission of Aquatic Rhabdoviruses," *Virology* 525:143-149 (2018), which are hereby incorporated by reference in their entirety). It was determined that XM-01 did not need light to inhibit pNiV infection. By contrast, the antiviral activity of LJ001 was severely reduced in the absence of light (FIG. 3D). This emphasizes a wider range of applications for XM-01 as a broad-spectrum antiviral.

Example 4—XM-01 Inhibits Membrane Fusion, but not Glycoprotein Function

Figures 4A, 4B, 4C:
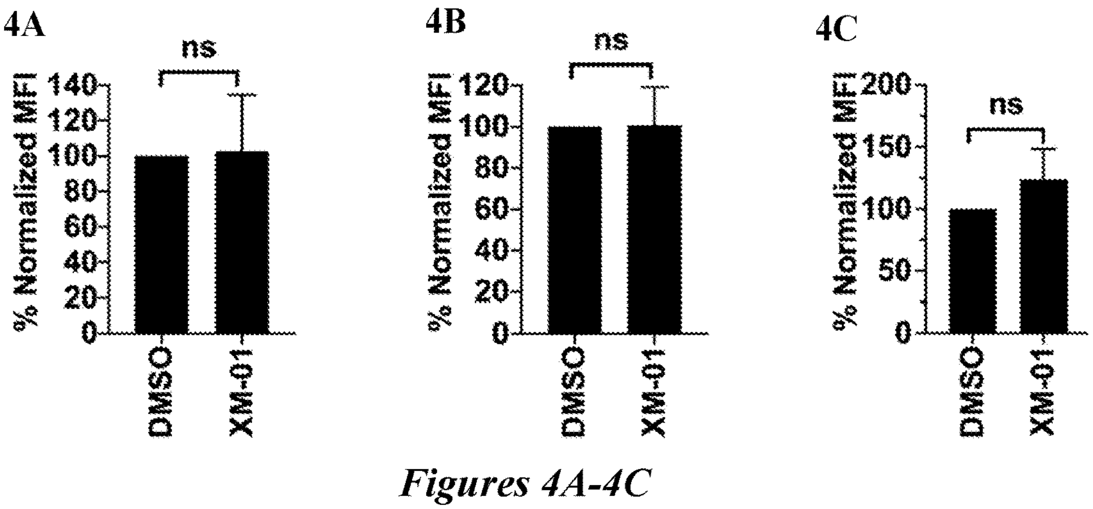
FIGS. 4A-4F depict that XM-01 inhibits membrane fusion without affecting the viral glycoproteins.

As modifications to glycoproteins can abrogate fusion, XM-01 was tested to see if it affects the viral glycoproteins. First, XM-01 was analyzed to determine whether it affected viral binding to the host receptor. HEK293T or PK13 cells were transfected with the NiV attachment glycoprotein (G) expression plasmid, followed by incubation of these cells with a mixture of soluble receptor ephrinB2 and XM-01. EphrinB2/G binding was then measured by flow cytometry. XM-01 did not interfere with the receptor-binding ability of the G glycoprotein (FIGS. 4A and 4B). Additionally, XM-01 was tested to see if it affected the NiV fusion glycoprotein's (F) ability to be triggered by G to execute membrane fusion. Using an HR2 peptide mimic of F labeled with Cy5, PK13 cells transfected with F and G were analyzed by flow cytometry to determine if F could still be triggered in the presence of XM-01 (Aguilar et al., "A Quantitative and Kinetic Fusion Protein-Triggering Assay Can Discern Distinct Steps in the Nipah Virus Membrane Fusion Cascade," *J. Virol.* 84:8033-8041 (2010), which is hereby incorporated by reference in its entirety). F-triggering was not decreased upon XM-01 treatment (FIG. 4C), indicating the preservation of both F and G glycoproteins in functional forms.

Figures 4D, 4E, 4F:
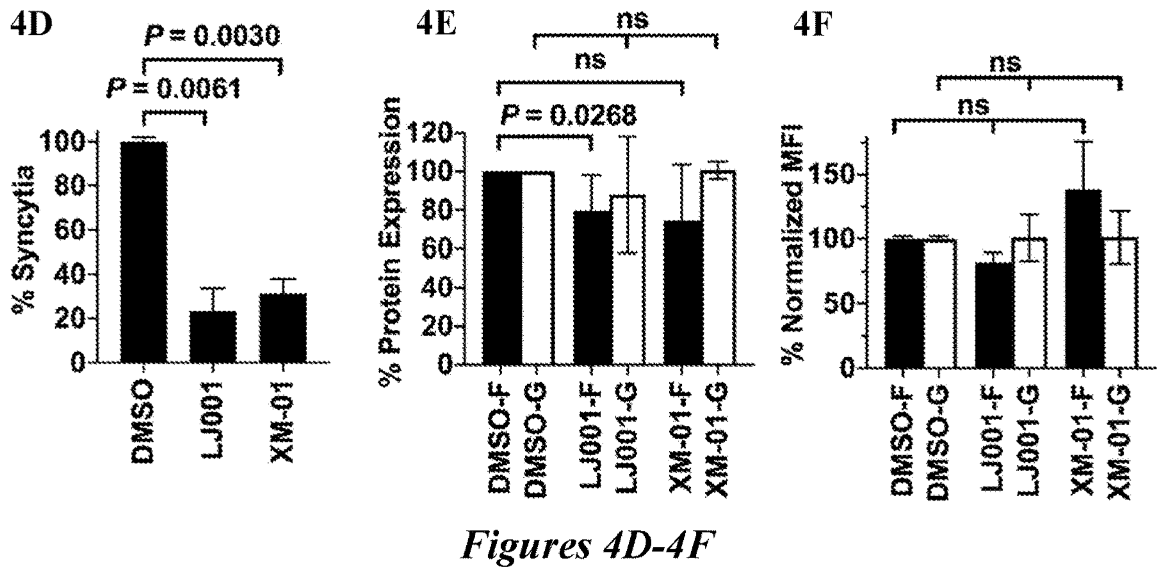

Since XM-01 did not affect the function of F or G, it was then tested whether XM-01 would affect cell-cell fusion executed by NiV glycoproteins. Syncytia formation quantification is a surrogate assay used to study cell-cell membrane fusion executed by paramyxoviral glycoproteins which is a significant pathological outcome of paramyxoviral infections and an important process for viral spread between infected and naïve cells. XM-01 treatment in cells expressing F and G significantly reduced levels of cell-cell membrane fusion (FIG. 4D). These results are consistent with XM-01 interfering with a step in the membrane fusion cascade, during viral entry. To corroborate that inhibition of cell-cell fusion by XM-01 was not due to a decrease in cell surface expression of the F and G glycoproteins, their levels of cell surface expression were measured by flow cytometry and were found to not be significantly affected (FIG. 4E).

Since XM-01 did not affect the binding or F-triggering steps of membrane fusion, it was then tested whether XM-01 affected the overall conformations of F or G. In this experiment, pNiV was incubated with XM-01 for 30 min before the compound was washed away with NTE buffer. Primary and secondary antibodies were incubated with treated virions to determine relative binding levels of two polyclonal antisera to F or G by flow virometry (Landowski et al., "Nipah Virion Entry Kinetics, Composition, and Conformational Changes Determined by Enzymatic Virus-Like Particles and New Flow Virometry Tools," *J. Virol.* 88:14197-14206 (2014), which is hereby incorporated by reference in its entirety) and observed no significant changes in antibody binding to either glycoprotein. LJ001 was used as a control, which is known to affect viral membranes, but not viral glycoprotein conformations (FIG. 4F). This data suggests that XM-01 affects the important process of membrane fusion, without significantly affecting glycoprotein functions.

Example 5—XM-01 Compromises Viral Membranes

Figure 5A:
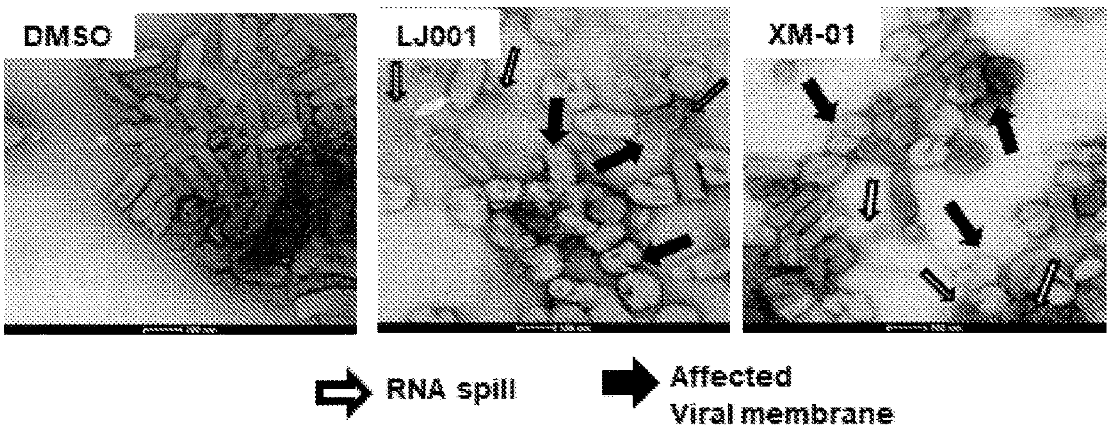
FIGS. 5A-5G depict that XM-01 compromised viral membrane fluidity.

XM-01 affects virus in a manner independent of binding or F-triggering and appeared to affect the virus particles directly while leaving glycoproteins intact. Furthermore, XM-01 affected several enveloped viruses tested, but not non-enveloped viruses. This suggested that XM-01 affects viral membranes. Therefore, the virus treated with XM-01 was imaged using electron microscopy to explore possible physical effects of XM-01. It was evident that most viral particles treated with XM-01 had compromised membranes as compared to the DMSO control (FIG. 5A). LJ001-treated pNiV was used to confirm that what was observed was the compromised membranes, as LJ001 is known to affect the viral membrane (Vigant et al., "A Mechanistic Paradigm for Broad-Spectrum Antivirals that Target Virus-Cell Fusion," *Plos Pathog.* 9(4):e1003297 (2013); Wolf et al., "A Broad-spectrum Antiviral Targeting Entry of Enveloped Viruses,"

Figure 5B:
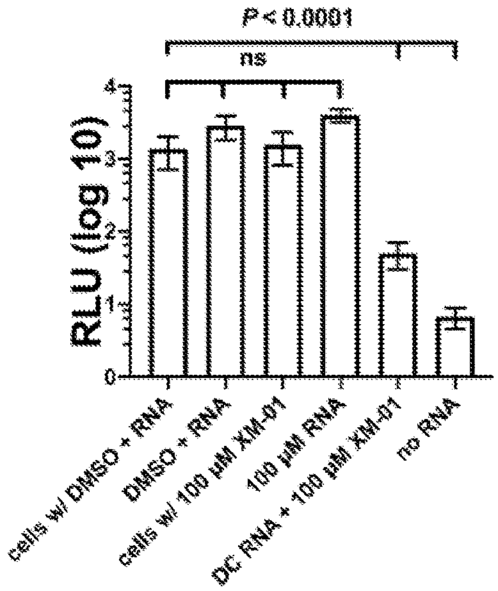

*PNAS* 107:3157-3162 (2010), which are hereby incorporated by reference in their entirety). RNA appeared to spill more frequently from virions treated with XM-01 and LJ001 as compared to the DMSO treated virions. Therefore, RNA was then tested to see if it was affected by XM-01 treatment. An nsp3: luciferase RNA construct was treated with XM-01 or vehicle control and electroporated into BHK cells. XM-01 did not alter the RNA stability relative to the DMSO control (FIG. 5B).

Figure 5C:
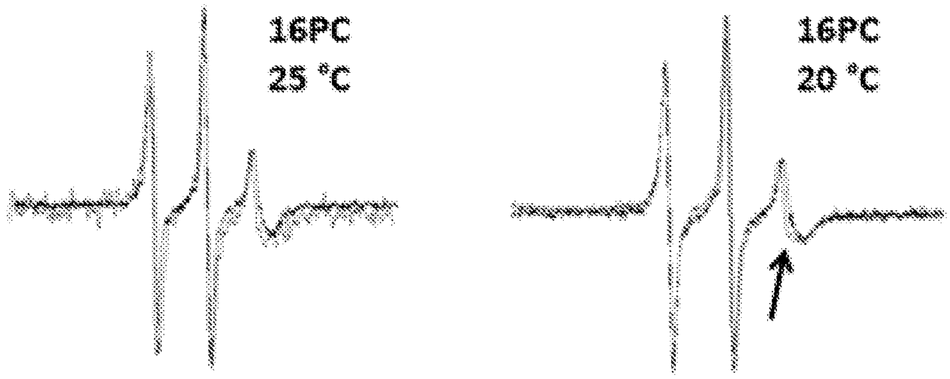
Figure 5D:
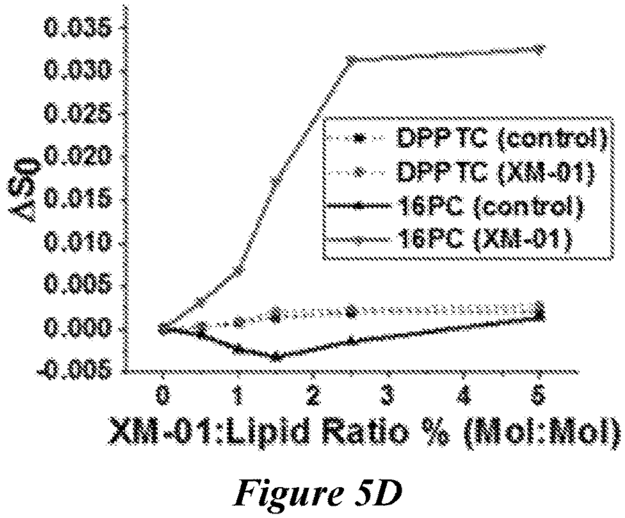

It was hypothesized that XM-01 intercalates into the viral membrane to inhibit viral fusion. To test this, electron spin resonance was performed on large multilamellar vesicles treated with XM-01. Spectral changes were detected upon XM-01 binding to the spin-labeled lipid 1-palmitoyl-2-(16-doxyl stearoyl) phosphatidylcholine (16-PC) (FIG. 5C). A shift of the high field peak, upon XM-01 binding, towards a lower frequency indicated that 16-PC was in a more hydrophobic environment. An equivalent comparison at 25° C. (FIG. 5C, right) shows a second component emerging upon XM-01 binding. This revealed that XM-01 intercalates deep into the hydrophobic region of the membrane.

To further understand the effect XM-01 induces on membrane structure, the lipid order was measured. The $\Delta S_0$ of the sample with and without XM-01 binding was calculated for XM-01: lipid ratios. A greater $S_0$ indicates a more ordered lipid alignment. It was observed that the membrane order in the headgroup region of dipalmitoyl phosphatidyl tempo (2,2,6,6-tetramethyl-1-oxy) choline (DPPTC) was unchanged upon XM-01 binding (FIG. 4D). However, in the deep hydrophobic region, XM-01 induced an increase in membrane order (up to 0.035 at 5%). Previously, it was found that a series of viral fusion peptides, including those from influenza, HIV, SARS CoV, and Dengue virus, induced membrane ordering in the headgroup and shallow hydrophobic regions, but not in the deep hydrophobic region, which promotes membrane fusion (Ge and Freed, "Fusion Peptide from Influenza Hemagglutinin Increases Membrane Surface Order: An Electron-Spin Resonance Study," *Biophys. J.* 96:4925-4934 (2009); Lai and Freed, "HIV gp41 Fusion Peptide Increases Membrane Ordering in a Cholesterol-Dependent Fashion," *Biophys. J.* 106:172-181 (2014); Lai and Freed, "The Interaction Between Influenza HA Fusion Peptide and Transmembrane Domain Affects Membrane Structure," *Biophys. J.* 109:2523-2536 (2015); Pinello et al., "Structure-function Studies Link Class II Viral Fusogens with the Ancestral Gamete Fusion Protein HAP2," *Curr. Biol.* 27:651-660 (2017); Lai et al., "The SARS-CoV Fusion Peptide Forms an Extended Bipartite Fusion Platform that Perturbs Membrane Order in a Calcium-Dependent Manner," *J. Mol. Biol.* 429:3875-3892 (2017), which are hereby incorporated by reference in their entirety). Importantly, and in contrast, the membrane ordering effect of XM-01 is opposite to those of the viral fusion peptides, i.e. it promotes ordering in the deep hydrophobic region.

Figure 5E:
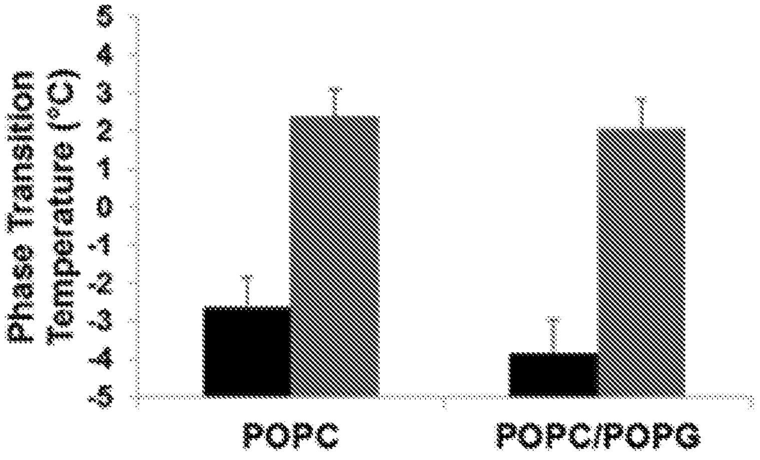

The effect on phase transition temperature induced by XM-01 was examined. By decreasing the temperature in 1° C. steps, the samples were monitored for the phase transition point. XM-01 increased the phase transition temperature of both pure POPC (5.3° C.) and POPC/POPG (4:1) (5.8° C.) membranes, indicating that XM-01 entering the membrane induced a greater tendency to turn the liquid-ordered phase into a more gel-ordered phase (FIG. 5E). This is consistent with the membrane ordering effect, and the effect of XM-01 decreasing membrane fusion. Altogether, this shows XM-01 intercalates in the deep hydrophobic region of the lipid bilayer, induces membrane ordering and increases the phase transition temperature of the membrane.

Figure 5F:
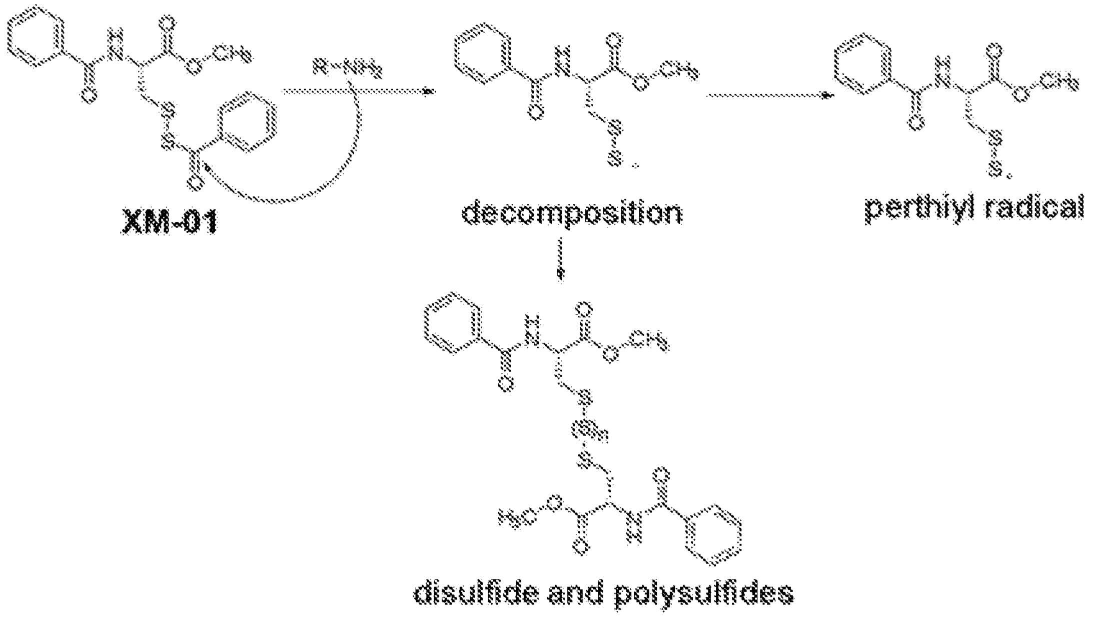
Figure 5G:
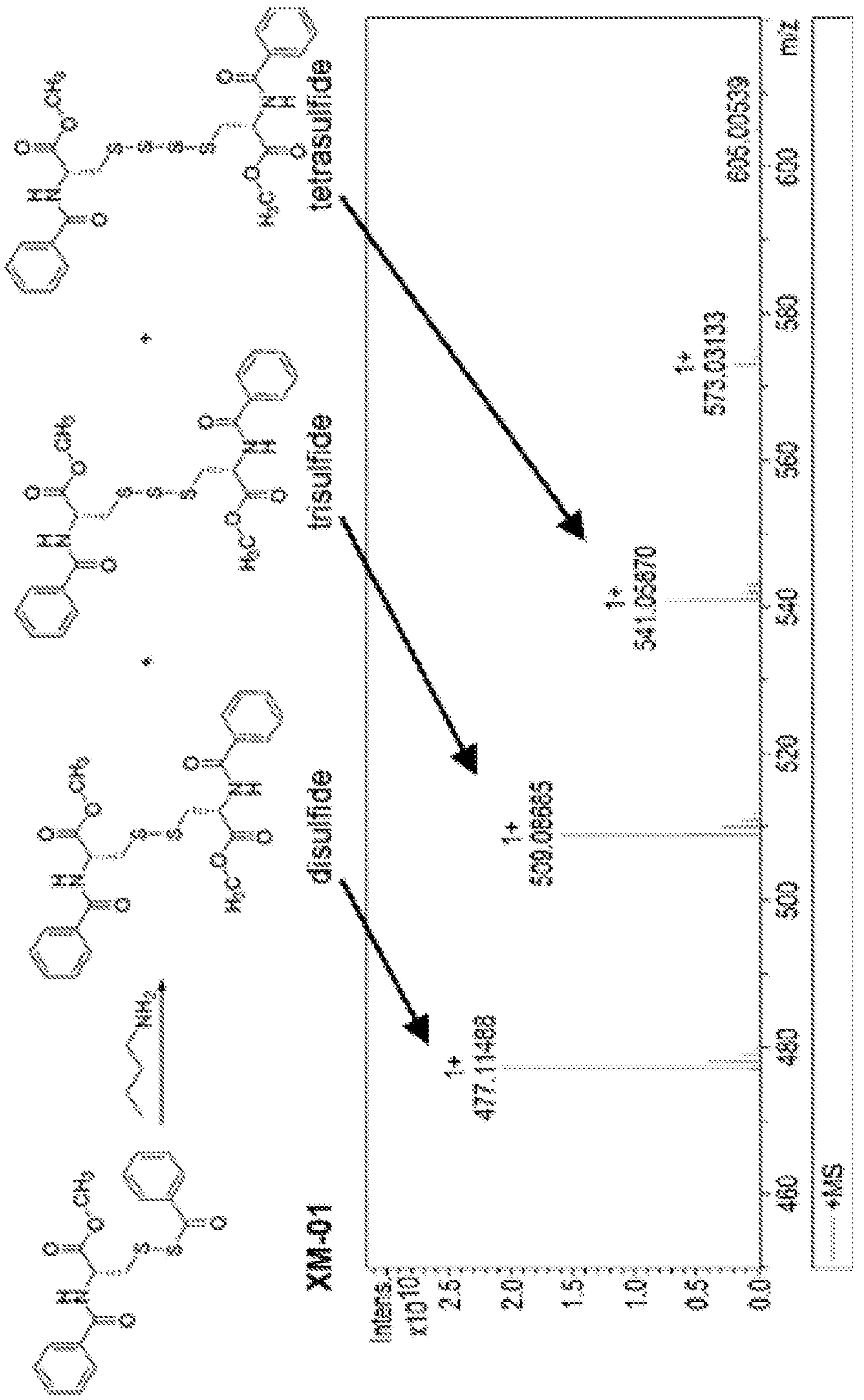

Next, the molecular transformation XM-01 undergoes to induce changes in membrane order was examined. Like other $H_2S$ donors, under physiological conditions, acyl groups on sulfur are transferred to nucleophiles such as amino acids and ultimately generate persulfides. Persulfides and hydropersulfides can be oxidized into perthiyl radicals (R—S—S.) (Bianco et al., "The Chemical Biology of the Persulfide (RSSH)/perthiyl (RSS) Redox Couple and Possible Role in Biological Redox Signaling," *Free Radic. Biol. Med.* 101:20-31 (2016), which is hereby incorporated by reference in its entirety). The reaction of XM-01 with butylamine in $CH_2Cl_2$ was analyzed. Cysteine polysulfides, the decomposition products of persulfides (FIGS. 5F and 5G) were recovered. In cellular environments, the generation of persulfides tends to produce radicals (Park et al., "Persulfides: Current Knowledge and Challenges in Chemistry and Chemical Biology," *Mol. Biosyst.* 11:1775-1785 (2015), which is hereby incorporated by reference in its entirety). This suggests that XM-01 and its perthiyl radical products may be inducing physical changes to the viral membrane by a radical mechanism.

Figure 6A:
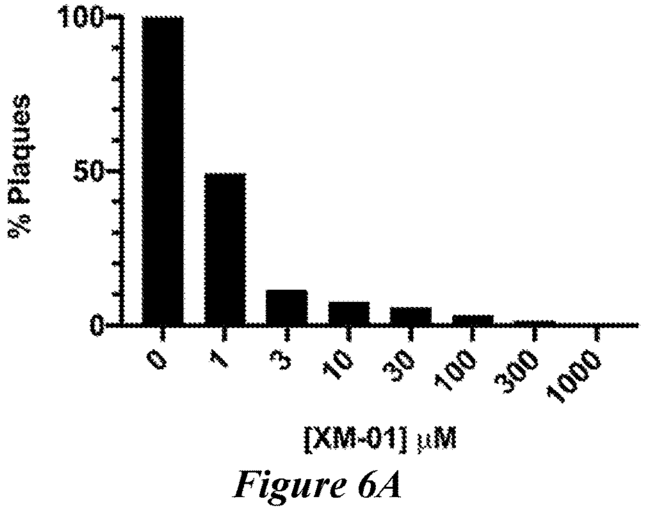
FIGS. 6A-6E depict that XM-01 inactivated H1N1 produces an effective vaccine.
Figure 6B:
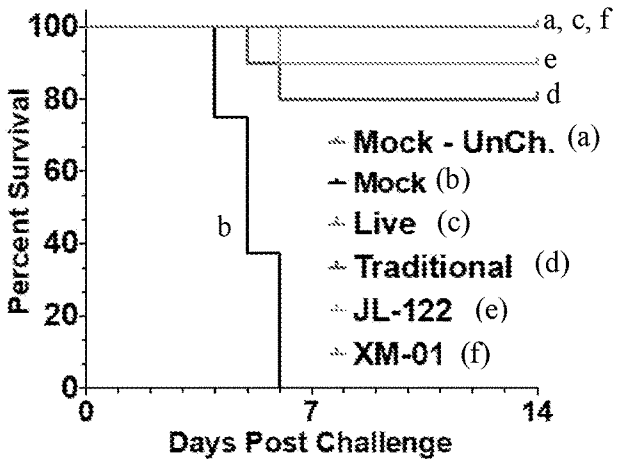
Figure 6C:
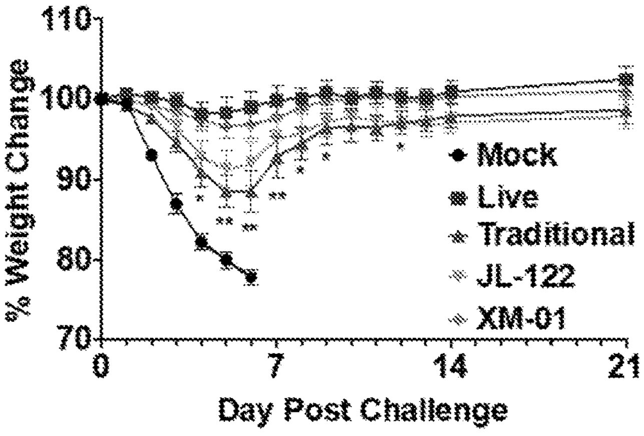
Figure 6D:
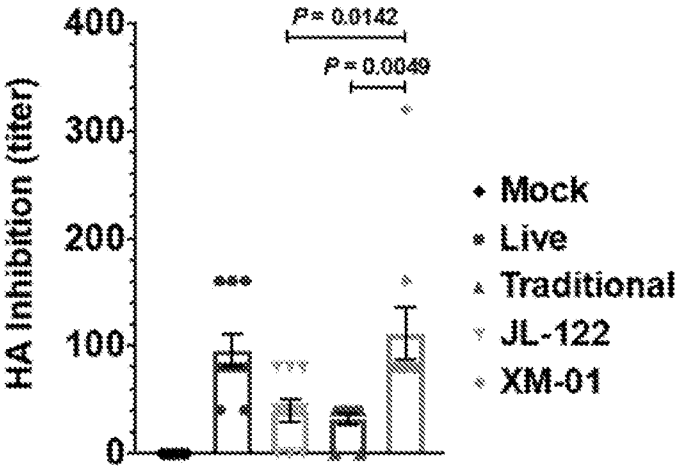
Figure 6E:
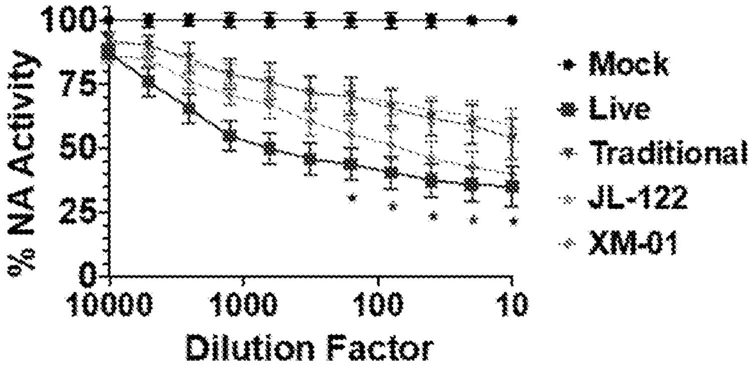
Figure 7A:
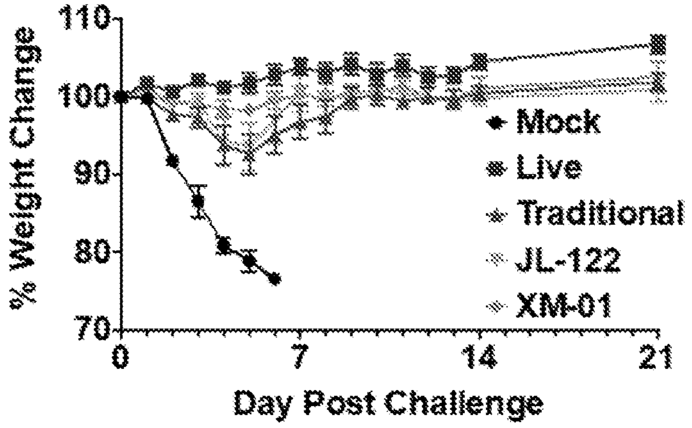
FIGS. 7A-7B depict the percent weight change after Ca/04/09 H1N1 challenge in vaccinated mice.
Figure 7B:
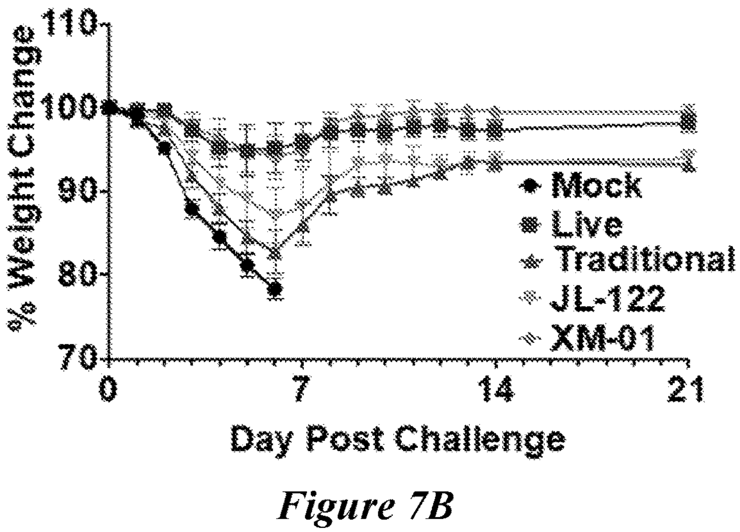
Figure 8A:
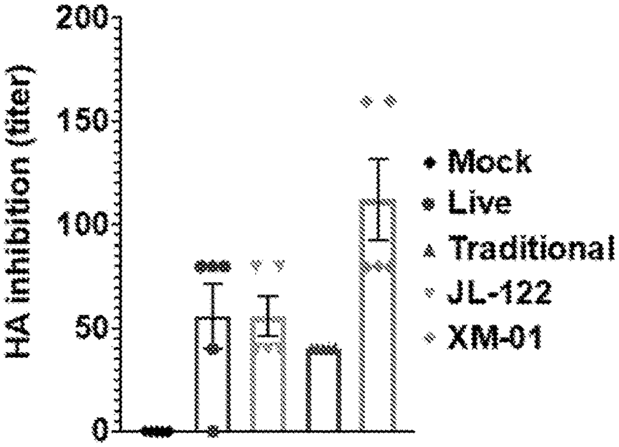
FIGS. 8A-8C depict the results of the hemagglutination inhibition assay with serum from vaccinated mice.
Figure 8B:
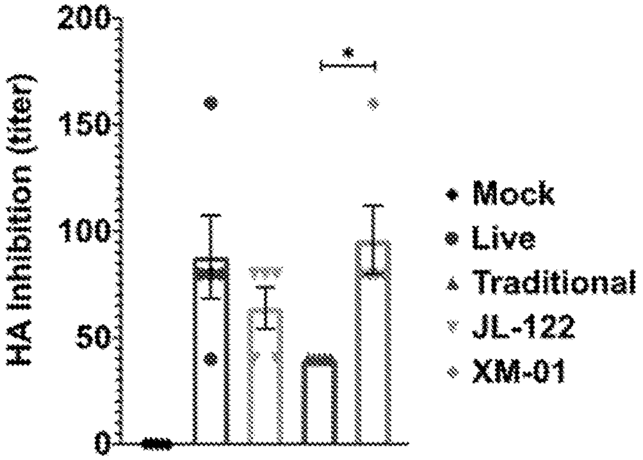
Figure 8C:
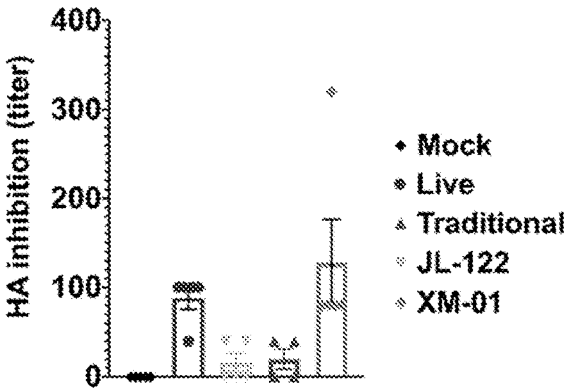
Figure 9A:
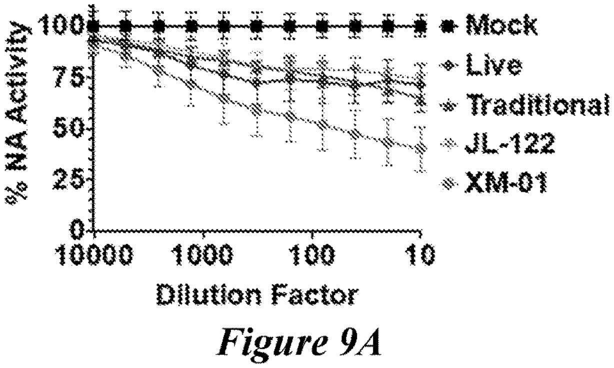
FIGS. 9A-9C depict the percent neuraminidase activity assay with serum from vaccinated mice after the second boost.
Figure 9B:
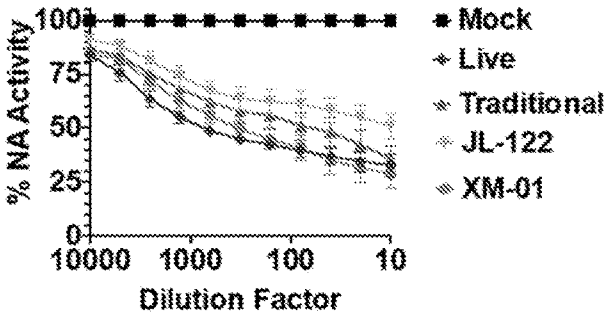
Figure 9C:
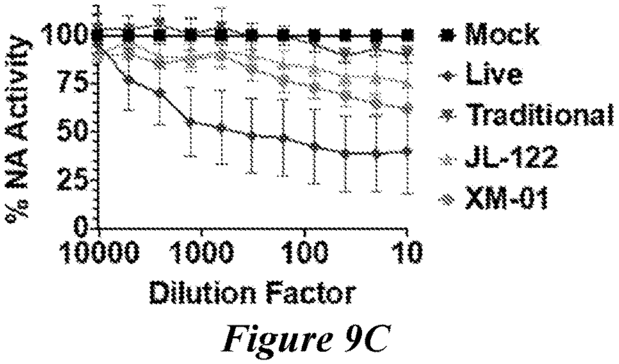

Example 6—XM-01-Inactivated Virus Vaccination Results in Strong Immune Responses The unique antiviral capabilities of XM-01 were utilized in production of an inactivated influenza virus (IIV) vaccine. First the inactivation of A/California/04/2009 (H1N1), a mouse adapted influenza strain, with XM-01 by plaque assays in MDCK cells was optimized. Infectivity was significantly inhibited by treating A/California/04/2009 with increasing concentrations of XM-01 for 4 h at room temperature and overnight at 4° C. The $EC_{50}$ was determined to be in the high nanomolar to low micromolar range (FIG. 6A). Treating influenza at $1\times10^5$ PFU/mL with 1 mM XM-01 in 1% DMSO for 4 h at RT resulted in complete neutralization, as confirmed through passage in cell culture, eggs, and plaque assays (FIG. 6A). Then, the ability of XM-01 to produce an IIV vaccine using A/California/04/2009 was tested. A/California/04/2009 was incubated with XM-01, JL-122, formalin, and a mock control for 4 h at room temperature before intramuscular vaccination of 1:1 alum/virus. Female and male mice, with 5 mice per group, received two additional boosts, separated by two weeks each. Mouse sera were assessed for antibodies raised against hemagglutinin and neuraminidase using hemagglutination (HI) and neuraminidase inhibition (NI) assays. The mice were challenged at $5LD_{50}$ of A/California/04/2009. All mice that received the XM-01-inactivated H1N1 survived the challenge, compared to the mock vaccinated mice which succumbed to the infection within six days post-challenge (FIG. 6B). Along with excellent survival, mice vaccinated with XM-01-inactivated virus also suffered significantly less weight loss compared to all other treatments, except for the live-virus vaccinated group (FIG. 6C). Interestingly, the female mice had reduced weight loss compared to the male mice that received formalin, JL-122, and XM-01 inactivated virus (FIGS. 7A and 7B). Then, the immune response toward the Ca/04/2009 H1N1 hemagglutinin glycoprotein with serum collected from vaccinated mice was tested. Using a hemagglutination inhibition assay, antibody titers against HA were determined by incubating A/California/04/2009 with sera from vaccinated mice for 45 min. This was then overlaid with 0.8% rooster blood and incubated for 45 min at room temperature before analysis. The XM-01-inactivated virus yielded a superior immune response toward HA, compared to the JL-122 and formalin-inactivated virus, and slightly better than the live-virus vaccinated mice (FIG. 6D). Additionally, while female mice had a better immune response toward HA than the male mice after three vaccinations with formalin and JL-122 inactivated virus, the sera results after 2 injections show that the XM-01 generated vaccine elicited the strongest response (FIGS. 8A-8C). Likewise, serum collected from vaccinated mice was tested to measure the immune response toward NA by measuring the enzymatic activity of a standard NA cleavage assay utilizing MuNANA (Leang and Hurt, "Fluorescence-based Neuraminidase Inhibition Assay to Assess the Susceptibility of Influenza Viruses to The Neuraminidase Inhibitor Class of Antivirals," *Journal of Visualized Experiments: JoVE* 55570 (2017), which is hereby incorporated by reference in its entirety). At increasing dilutions, serum from mice vaccinated with XM-01-inactivated virus displayed superior neutralization compared to JL-122 and formaldehyde-inactivated H1N1, but not the live-virus vaccinated mice (FIG. 6E). However, female mouse serum had better NA neutralization activity than the male mice when vaccinated with formalin, JL-122, and XM-01 inactivated virus (FIG. 9A-9C). This result was incredibly surprising as most conventional IIVs do not induce such a strong immune response towards NA (Wohlbold et al., "Vaccination With Adjuvanted Recombinant Neuraminidase Induces Broad Heterologous, But Not Heterosubtypic, Cross-protection Against Influenza Virus Infection in Mice," *MBio* 6:e02556 (2015), which is hereby incorporated by reference in its entirety). Overall, the data revealed that XM-01 inactivated the virus by physically changing the viral membrane while leaving the glycoproteins intact. This in turn allowed for the creation of an effective vaccine that can completely protect mice from a lethal challenge and generate a potent immune response, especially compared to viruses inactivated with traditional methods (Kon et al., "Influenza Vaccine Manufacturing: Effect of Inactivation, Splitting and Site of Manufacturing. Comparison of Influenza Vaccine Production Processes," *PLoS One* 11:e0150700 (2016), which is hereby incorporated by reference in its entirety).

Example 7—XM-01 Inactivated Murine Hepatitis Virus

Figure 10:
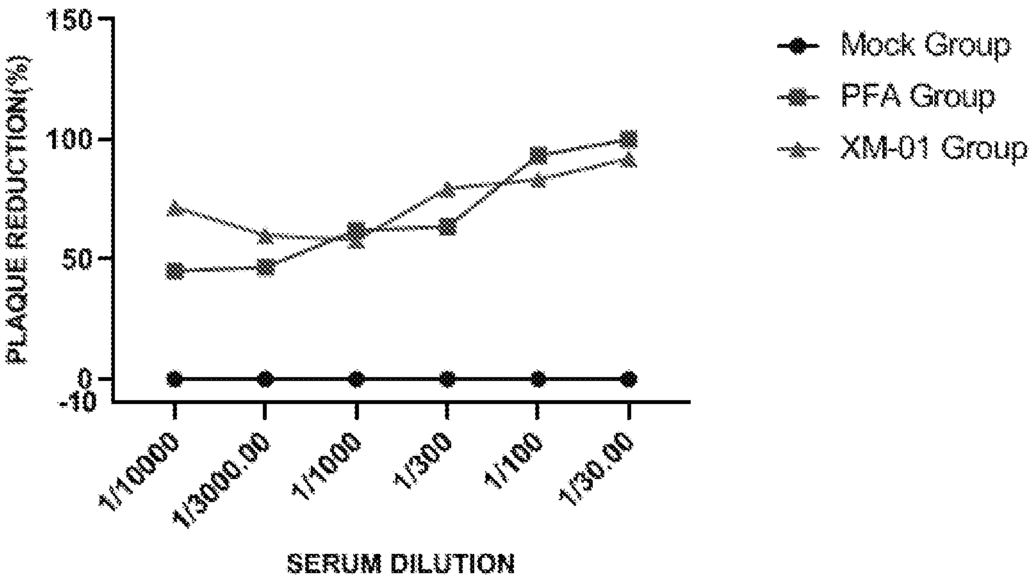
FIG. 10 is a graphical analysis of a plaque reduction neutralization test (PRNT) assay using mouse sera against the murine hepatitis virus (Murine Coronavirus strain A59, MHV-A59) after 2 vaccinations.

Murine hepatitis virus (murine coronavirus stain A59, MHV-A59) was inactivated with XM-01 and mice were vaccinated two times separated by 3 weeks between vaccination. Sera taken two weeks after the second vaccination was used to conduct a plaque reduction neutralization test (PRNT) showing the generation of neutralizing antibodies against MHV (FIG. 10).

Example 8—Plaque Assay for Measurement of SARS-CoV-2 Coronavirus Infections

Figure 11:
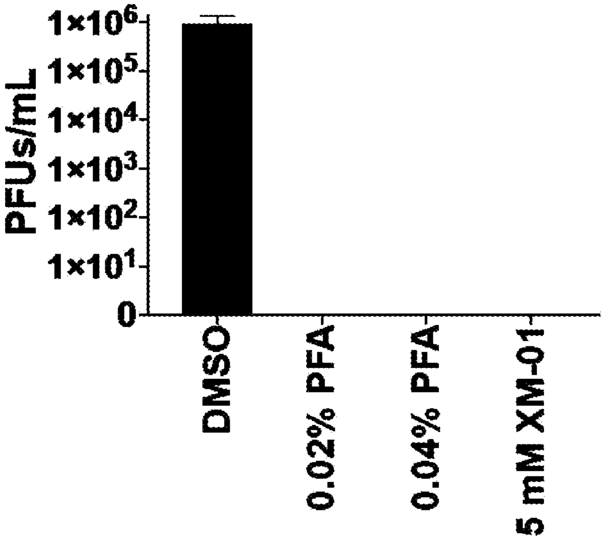
FIG. 11 depict the complete inactivation of SARS-CoV-2 at a 5 mM concentration of XM-01 as well as 0.02 and 0.04% formalin as determined via plaque assay. The virus was propagated by incubating VeroE6 cells with 0.01 MOI of SARS-CoV-2 (isolate USA-WA1/2020, BEI resources cat #NR-52281) for 48 h. The virus was then treated for 48 h at room temperature with 5 mM XM-01, PFA, or mock (DMSO only), n=3 error bars represent ±SD.

SARS-CoV-2 virus (isolate USA-WA1/2020, BEI resources cat #NR-52281) was treated with DMSO, 1-5 mM XM-01, or 0.02% PFA for 48 h at room temperature. Treated dilutions of virus were titrated on Vero E6 cells using standard plaque assay, plaque forming units stained with crystal violet and counted 3 days post-infection. XM-01 was effective to inhibit plaque formation of SARS-CoV2 when the virons were treated with XM-01, as shown in FIG. 11.

Discussion of Examples 1-8

It has been reported that XM compounds have robust inhibitory properties against enveloped viruses. This led to the exploration XM-01 as a potential broad-spectrum antiviral against enveloped viruses such as NiV, VSV, RSV, HCMV, HSV-1, and influenza viruses. However, the non-enveloped rota- and norovirus were not inhibited. Compounds XM-01, 02, 03, 10, and 11 (FIG. 1A) all possess inhibitory properties and displayed low levels of cytotoxicity (FIG. 1B); importantly, XM-01 exhibited low cytotoxicity levels as compared to other sulfur-containing compounds tested in this study, with a selectivity index ($CC_{50}$/$EC_{50}$ ratio) for XM-01 of about 1,000 (FIGS. 1 and 2). The inhibitory activity of XM-01 is not likely caused by $H_2S$ release as compared to NaHS or GYY4137 (FIG. 1A), of which inhibitory activity is attributed to $H_2S$ release (Li et al., "Role of Hydrogen Sulfide in Paramyxovirus Infections," *J. Virol.* 89:5557-5568 (2015); Zhao et al., "Controllable Hydrogen Sulfide Donors and Their Activity Against Myocardial Ischemia-Reperfusion Injury," *ACS Chem. Biol.* 8:1283-1290 (2013), which are hereby incorporated by reference in their entirety). The data indicate that XM-01 is a more potent antiviral inhibitor than NaHS or GYY4137. By contrast, the $EC_{50}$ of GYY4137 is 10 mM (Li et al., "Role of Hydrogen Sulfide in Paramyxovirus Infections," *J. Virol.* 89:5557-5568 (2015), which is hereby incorporated by reference in its entirety), ~4 orders of magnitude greater than that of XM-01 (FIG. 1A) (Li et al., "Role of Hydrogen Sulfide in Paramyxovirus Infections," *J. Virol.* 89:5557-5568 (2015); Li et al., "Characterization of a Novel, Water-Soluble Hydrogen Sulfide-Releasing Molecule (GYY4137): New Insights into the Biology of Hydrogen Sulfide," *Circulation* 117:2351-2360 (2008); Lee et al., "The Slow-Releasing Hydrogen Sulfide Donor, GYY4137, Exhibits Novel Anti-Cancer Effects In Vitro and In Vivo," *Plos One* 6(6):e21077 (2011); Zhao et al., "Hydrogen Sulfide ($H_2S$) Releasing Agents: Chemistry and Biological Applications." *Chem. Comm.* 50:11788-11805 (2014), which are hereby incorporated by reference in its entirety).

Importantly, XM-01 does not need light to inhibit enveloped virus infections, as opposed to the broad-spectrum antiviral LJ001 (FIG. 3). While LJ001 is being explored as an inhibitor of viral transmission in fish aquaculture (Balmer et al., "Inhibition of an Aquatic Rhabdovirus Demonstrates Promise of a Broad-Spectrum Antiviral for Use in Aquaculture," *J. Virol.* 91(4): e02181 (2017); Vigant et al., "A Mechanistic Paradigm for Broad-spectrum Antivirals That Target Virus-Cell Fusion," *PLoS Pathog* 9:e1003297 (2013), which are hereby incorporated by reference in their entirety), for the majority of the body where light does not penetrate, XM compounds are a better option. Therefore, these compounds represent a new class of broad-spectrum antivirals that inhibit viral membranes in a light-independent manner. It is herein demonstrated that XM-01 did not alter the viral glycoproteins or impair their functions tested but inhibited viral entry by reducing the fluidity of the viral membrane (FIGS. 4 and 5). Since XM-01 and its derivatives target a critical step in viral entry, membrane fusion, they have the necessary attributes for potential use as antiviral agents against enveloped viruses.

While the mechanism(s) by which XM-01 inhibits cell-cell and virus-cell fusion require further elucidation, structural comparison of the active vs inactive compounds tested revealed that all antiviral XM compounds have a unique acyl disulfide core structure (FIG. 1). Precisely how the core structure is involved in inhibiting the viral membrane requires further investigation and may be due to several factors. One could be that the core structure has the correct conformation to fit in the viral membrane, affecting membrane fluidity. Alternatively, the core structure may be releasing a reactive chemical species that acts directly on membrane lipids. Further investigation will be conducted to determine the exact mechanism of action to guide rational design of XM derivatives with greater activity.

XM-01 appears to affect viral membranes while leaving surface glycoproteins and RNA intact as measured via receptor binding, conformational changes, attachment and fusion glycoprotein function, and RNA stability (FIGS. 4 and 5). It was observed that XM-01 intercalates deep into the lipid bilayer and decompose into various persulfide species capable of producing radicals. Furthermore, it was determined that XM-01 ultimately increases membrane rigidity deep within the membrane and increases phase transition temperature. Altogether, this indicates that XM-01 does not affect important cellular proteins, which may explain its low cytotoxicity levels. Cells have an impressive capacity to repair their membranes (Cooper and McNeil, "Membrane Repair: Mechanisms and Pathophysiology," *Physiol. Rev.* 95:1205-1240 (2015), which is hereby incorporated by reference in its entirety). This also means that viral genes (all encoding for viral proteins) are less likely to undergo mutations to render viruses resistant to this type of compound, as compared to antiviral inhibitors that target viral proteins. It is also unlikely that a virus would be able to mutagenize its genes to modify the viral membrane, which is cell-derived, which would be the only likely way to create viral resistance to a membrane perturbing compound.

Finally, it was demonstrated that mice vaccinated with XM-01-inactivated virus survived 5×$LD_{50}$ challenge of A/California/04/2009 with less weight loss than traditional formalin-inactivated and JL-122-inactivated vaccines. The protection afforded by XM-01-inactivated virus matched that of the live-virus which, would ideally yield the strongest immune response. This coincided with the generation of potent anti-HA antibodies post-vaccination in the XM-01 mice. It was observed that antibodies inhibiting NA activity were greatest in the live-injected and XM-01 mice showing significantly better response compared to the formalin and JL122-inactivated groups (FIG. 6). Several studies have revealed that formalin-inactivation of viruses abrogates the immunogenicity of antigenic sites, resulting in nonprotective antibodies (Murphy and Walsh, "Formalin-inactivated Respiratory Syncytial Virus Vaccine Induces Antibodies to the Fusion Glycoprotein That Are Deficient in Fusion-inhibiting Activity," *J. Clin. Microbiol.* 26:1595-1597 (1988); Duque et al., "Effects of Formalin Inactivation on Bovine Herpes Virus-1 Glycoproteins and Antibody Response Elicited by Formalin-Inactivated Vaccines in Rabbits," *Vaccine* 7:513-520 (1989); Fan et al., "Formalin Inactivation of Japanese Encephalitis Virus Vaccine Alters the Antigenicity and Immunogenicity of a Neutralization Epitope in Envelope Protein Domain III," *PLoS Neglected Tropical Diseases* 9:e0004167-e0004167 (2015), which are hereby incorporated by reference in their entirety). Furthermore, in general, the female mice had superior protection in terms of weight loss and humoral immune response toward HA and NA glycoproteins than the males, which is a common result in mice vaccinated with influenza virus due to greater B cell activation and antibody production (FIGS. 7-9) (Lorenzo et al., "Antibody Responses and Cross Protection Against Lethal Influenza A Viruses Differ Between the Sexes in C57BL/6 Mice," *Vaccine* 29"9246-9255 (2011); Fink et al., "Biological Sex Affects Vaccine Efficacy and Protection Against Influenza in Mice," *PANS* 115:12477 (2018), which are hereby incorporated by reference in their entirety). The results also indicate that the female mice showed a stronger response to XM-01 inactivated vaccines after 2 vaccinations resulting in higher anti-HA and NA titers than even the live virus vaccinated group (FIGS. 8A-8C). This is another promising feature that indicates XM-01 derived vaccines may allow for higher seroconversion rates and use in immune-compromised populations.

Due to health and economic burdens enveloped viruses cause during global pandemics, the development of broad-spectrum membrane fusion inhibitors is of critical importance. XM-01 and its derivatives represent a new class of antiviral compounds with the potential to become the next-generation broad-spectrum antivirals for enveloped virus therapy. Furthermore, the mechanism of action studies may lead to future derivatives that possess even better antiviral activity. Importantly, since XM-01 does not affect viral glycoproteins functions or conformations, XM compounds hold promise as chemical inactivators for vaccine development, as conformationally intact viral glycoproteins are naturally excellent at eliciting immune responses, and current methods of inactivation can yield inconsistent results (Kon et al., "Influenza Vaccine Manufacturing: Effect of Inactivation, Splitting and Site of Manufacturing. Comparison of Influenza Vaccine Production Processes," *PLoS One* 11:e0150700 (2016); Delrue et al., "Inactivated Virus Vaccines from Chemistry to Prophylaxis: Merits, Risks and Challenges," *Expert Rev. Vaccines* 11:695-719 (2012); Astill et al., "Examination of the Effects of Virus Inactivation Methods on the Induction of Antibody- and Cell-Mediated Immune Responses Against Whole Inactivated H9N2 Avian Influenza Virus Vaccines in Chickens," Vaccine 36:3908-3916 (2018), which are hereby incorporated by reference in their entirety).

Enveloped viruses cause devastating zoonotic diseases and are the pathogens most likely to cause global pandemics. Sulfur-based compounds that target membranes, membrane fusion, and viral entry and possess broad-spectrum inhibitory properties against many pathogenic enveloped viruses tested were identified. The mechanism of inhibition was probed via multidisciplinary approaches that analyzed glycoprotein conformations, membrane fluidity, cell-cell fusion, viral entry, viral structure, and viral infectivity. These antivirals increase membrane order deep within the hydrophobic region of the bilayer and increase the membrane phase transition temperature, while leaving glycoproteins unaffected. The method of inactivation was tested to determine if it would be ideal for enveloped virus vaccine development, using one of the lead compounds, XM-01. An inactivated H1N1 influenza A/CA/04/2009 vaccine was developed and tested it in mice. As compared to the traditional formalin-inactivated H1N1 vaccine control, the XM-01-inactivated vaccine conferred reduced morbidity and mortality upon viral challenge, as well as statistically significantly enhanced immune responses to both HA and NA glycoproteins. In addition, an adjuvating effect for the XM-01 treated viral particles was observed. Surprisingly, this vaccine yielded even better humoral immune responses as compared to live intramuscular virus injections. Thus, herein is presented a new series of compounds that possess ideal properties to generate highly potent vaccines for enveloped viruses In summary, these results demonstrate that XM compounds can effectively inactivate viruses by physically changing the membrane while leaving the viral glycoproteins intact producing an excellent vaccine. The ability to deliver unaltered viral glycoproteins, with immunogenic sites intact, is paramount in creating a potent immune response against enveloped viruses. The XM-01 inactivated-virus study serves as an exemplar vaccination approach in the generation of prospective vaccines for zoonotic viruses that pose a significant threat to public health.

Although preferred embodiments have been depicted and described in detail herein, it will be apparent to those skilled in the relevant art that various modifications, additions, substitutions, and the like can be made without departing from the spirit of the application and these are therefore considered to be within the scope of the application as defined in the claims which follow.

What is claimed:

1. A method of vaccinating a subject against infection by an enveloped virus, said method comprising:

providing a compound of the Formula (I):

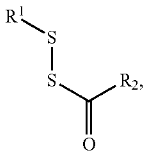

(I)

wherein $R^1$ is

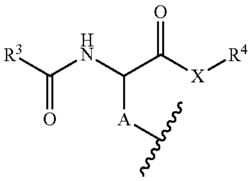

or —C(O)Ph, $R^2$ is $C_{1-6}$ alkyl or aryl;

$R^3$ is $C_{1-6}$ alkyl or aryl;

$R^4$ is $C_{1-6}$ alkyl optionally substituted with aryl;

A is $C_{1-3}$ alkylene;

X is O or NH; and

is the point of attachment of $R^1$ to S;

contacting the compound of Formula (I) with an isolated enveloped virus, having a membrane, to inactivate the membrane of the isolated enveloped virus; and treating the subject with the enveloped virus having an inactivated membrane to vaccinate the subject against the enveloped virus.

2. The method of claim 1, when A is $—CH_2—CH_2—$, X is NH, and $R^4$ is n-butyl, $R^2$ is not methyl.

3. The method of claim 1, wherein if $R^1$ is —C(O)Ph, then $R^2$ is aryl.

4. The method of claim 1, wherein $R^2$ is Me or Ph.

5. The method of claim 1, wherein $R^3$ is Me or Ph.

6. The method of claim 1, wherein $R^4$ is Me, $—CH_2$-Ph, or n-butyl.

7. The method of claim 1, wherein the compound of Formula (I) is selected from the group consisting of:

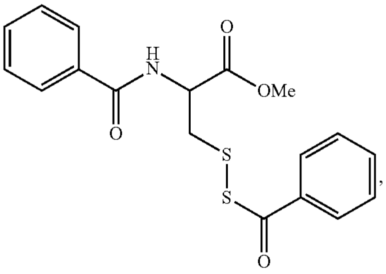

,

-continued

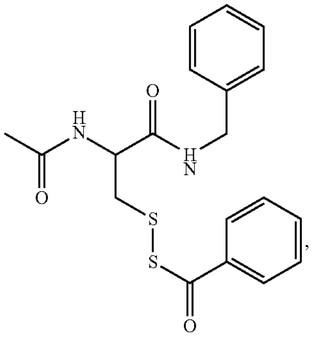

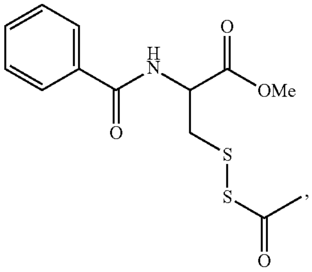

-continued

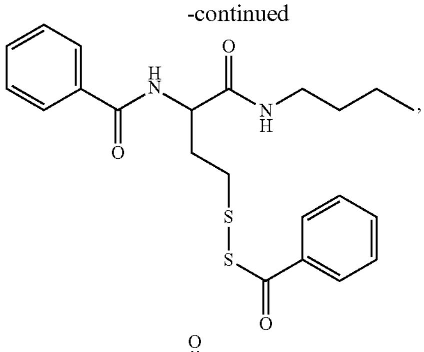

and

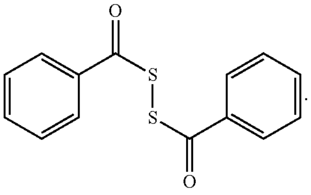

8. The method of claim 1 further comprising: selecting a subject in need of vaccination against infection by an enveloped virus.

9. The method of claim 1, wherein the enveloped virus is selected from the group consisting of Ebola virus, human immunodeficiency virus, influenza virus, Lassa fever virus, Nipah virus, respiratory syncytial virus, Rift Valley fever virus, SARS virus, MERS virus, Marbury virus, swine pox virus, Cytomegalovirus, Crimean hemorrhagic fever virus, and COVID-19.

10. The method of claim 1, wherein the enveloped virus is selected from the group consisting of herpesviruses, poxviruses, hepadnaviruses, asfarviridae, flavivirus, alphavirus, togavirus, coronavirus, hepatitis viruses, orthomyxovirus, paramyxovirus, rhabdovirus, bunyavirus, Filovirus, and retroviruses.

* * * * *